(12) United States Patent
Chu et al.

(10) Patent No.: US 7,524,281 B2
(45) Date of Patent: Apr. 28, 2009

(54) SYSTEMS AND METHODS RELATING TO ASSOCIATING A MEDICAL IMPLANT WITH A DELIVERY DEVICE

(75) Inventors: Michael S. H. Chu, Brookline, MA (US); Brian M. Hanley, Framingham, MA (US); Alfred Intoccia, Amherst, NH (US); Richard C. Tah, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 439 days.

(21) Appl. No.: 10/991,906

(22) Filed: Nov. 17, 2004

(65) Prior Publication Data

US 2005/0177022 A1    Aug. 11, 2005

Related U.S. Application Data

(60) Provisional application No. 60/523,208, filed on Nov. 17, 2003.

(51) Int. Cl.
*A61F 13/00* (2006.01)
(52) U.S. Cl. ........................................ 600/37
(58) Field of Classification Search ............... 600/30, 600/37, 29, 114; 606/1, 119, 139, 151, 190, 606/191, 148, 222, 228; 128/885; 602/4, 602/523
See application file for complete search history.

(56) References Cited

U.S. PATENT DOCUMENTS

| | | |
|---|---|---|
| 3,565,073 A | 2/1971 | Giesy |
| 3,704,712 A | 12/1972 | Giesy et al. |
| 4,798,193 A | 1/1989 | Giesy et al. |
| 4,824,435 A | 4/1989 | Giesy et al. |
| 4,872,451 A | 10/1989 | Moore et al. |
| 4,946,467 A | 8/1990 | Ohi et al. |
| 4,946,468 A | 8/1990 | Li |
| 5,002,550 A | 3/1991 | Li |
| 5,064,435 A | 11/1991 | Porter |
| 5,078,730 A | 1/1992 | Li |
| 5,084,058 A | 1/1992 | Li |
| 5,087,263 A | 2/1992 | Li |
| 5,112,344 A | 5/1992 | Petros |
| 5,152,749 A | 10/1992 | Giesy et al. |
| 5,207,679 A | 5/1993 | Li |
| 5,250,033 A | 10/1993 | Evans et al. |
| 5,256,150 A | 10/1993 | Quiachon et al. |

(Continued)

FOREIGN PATENT DOCUMENTS

DE    10103179    7/2001

(Continued)

OTHER PUBLICATIONS

Fianu et al Absorbable Polyglactin Mesh for Retropubic Sling Operation in Female Urinary Stress Incontinence. Gynecol. obstet. Invest. 16:45-50 (1983).

(Continued)

*Primary Examiner*—Samuel G Gilbert
(74) *Attorney, Agent, or Firm*—Ropes & Gray LLP

(57) ABSTRACT

The present invention provides devices and methods for associating an implantable sling with a delivery device for delivering the sling to an anatomical location in a patient.

18 Claims, 25 Drawing Sheets

U.S. PATENT DOCUMENTS

| | | | |
|---|---|---|---|
| 5,334,185 | A | 8/1994 | Giesy et al. |
| 5,368,595 | A | 11/1994 | Lewis |
| 5,383,904 | A | 1/1995 | Totakura et al. |
| 5,395,349 | A | 3/1995 | Quiachon et al. |
| 5,439,467 | A | 8/1995 | Benderev et al. |
| 5,456,722 | A | 10/1995 | McLeod et al. |
| 5,505,735 | A | 4/1996 | Li |
| 5,540,703 | A | 7/1996 | Barker, Jr. et al. |
| 5,611,515 | A | 3/1997 | Benderev et al. |
| 5,645,589 | A | 7/1997 | Li |
| 5,683,418 | A | 11/1997 | Luscombe et al. |
| 5,690,649 | A | 11/1997 | Li |
| 5,702,215 | A | 12/1997 | Li |
| 5,742,943 | A | 4/1998 | Chen |
| 5,749,884 | A | 5/1998 | Benderev et al. |
| 5,840,011 | A | 11/1998 | Landgrebe et al. |
| 5,860,993 | A | 1/1999 | Thompson et al. |
| 5,899,906 | A | 5/1999 | Schenk |
| 5,934,283 | A | 8/1999 | Willem et al. |
| 5,935,122 | A | 8/1999 | Fourkas et al. |
| 5,954,057 | A | 9/1999 | Li |
| 6,039,686 | A | 3/2000 | Kovac |
| 6,042,534 | A | 3/2000 | Gellman et al. |
| 6,050,937 | A | 4/2000 | Benderev |
| 6,053,935 | A | 4/2000 | Brenneman et al. |
| 6,096,041 | A | 8/2000 | Gellman et al. |
| 6,099,547 | A | 8/2000 | Gellman et al. |
| 6,200,330 | B1 | 3/2001 | Benderev et al. |
| 6,221,084 | B1 * | 4/2001 | Fleenor ............ 606/148 |
| 6,264,676 | B1 | 7/2001 | Gellman et al. |
| 6,273,852 | B1 | 8/2001 | Lehe et al. |
| 6,382,214 | B1 | 5/2002 | Raz et al. |
| 6,406,423 | B1 | 6/2002 | Scetbon |
| 6,423,080 | B1 | 7/2002 | Gellman et al. |
| D466,213 | S | 11/2002 | Snitkin et al. |
| 6,475,139 | B1 | 11/2002 | Miller |
| 6,478,727 | B2 | 11/2002 | Scetbon |
| 6,491,703 | B1 | 12/2002 | Ulmsten |
| 6,494,887 | B1 | 12/2002 | Kaladelfos |
| 6,530,943 | B1 | 3/2003 | Hoepffner et al. |
| 6,582,443 | B2 | 6/2003 | Cabak et al. |
| 6,596,001 | B2 | 7/2003 | Stormby et al. |
| 6,596,002 | B2 | 7/2003 | Therin et al. |
| 6,599,235 | B2 | 7/2003 | Kovac |
| 6,605,097 | B1 | 8/2003 | Lehe et al. |
| 6,612,977 | B2 | 9/2003 | Staskin et al. |
| 6,638,209 | B2 | 10/2003 | Landgrebe |
| 6,638,210 | B2 | 10/2003 | Berger |
| 6,638,211 | B2 | 10/2003 | Suslian et al. |
| 6,641,525 | B2 | 11/2003 | Rocheleau et al. |
| 6,648,921 | B2 | 11/2003 | Anderson et al. |
| 6,652,450 | B2 | 11/2003 | Neisz et al. |
| 6,685,629 | B2 | 2/2004 | Therin |
| 6,755,781 | B2 | 6/2004 | Gellman |
| 6,802,807 | B2 | 10/2004 | Anderson et al. |
| 6,830,052 | B2 | 12/2004 | Carter et al. |
| 2002/0072694 | A1 | 6/2002 | Snitkin |
| 2002/0077526 | A1 | 6/2002 | Kammerer et al. |
| 2002/0116025 | A1 | 8/2002 | Haab |
| 2002/0128670 | A1 | 9/2002 | Ulmsten et al. |
| 2002/0138025 | A1 | 9/2002 | Gellman et al. |
| 2002/0147382 | A1 | 10/2002 | Neisz et al. |
| 2002/0151910 | A1 | 10/2002 | Gellman et al. |
| 2002/0161382 | A1 | 10/2002 | Neisz et al. |
| 2003/0004580 | A1 | 1/2003 | Sump et al. |
| 2003/0009181 | A1 | 1/2003 | Gellman et al. |
| 2003/0010929 | A1 | 1/2003 | Priewe et al. |
| 2003/0023135 | A1 | 1/2003 | Ulmsten et al. |
| 2003/0028075 | A1 | 2/2003 | Ulmsten et al. |
| 2003/0050530 | A1 | 3/2003 | Neisz et al. |
| 2003/0065246 | A1 | 4/2003 | Inman et al. |
| 2003/0100954 | A1 | 5/2003 | Schuldt-Hempe et al. |
| 2003/0130670 | A1 | 7/2003 | Anderson et al. |
| 2003/0149440 | A1 | 8/2003 | Kammerer et al. |
| 2003/0171644 | A1 | 9/2003 | Anderson et al. |
| 2003/0176762 | A1 | 9/2003 | Kammerer |

FOREIGN PATENT DOCUMENTS

| | | |
|---|---|---|
| SU | 1225547 | 4/1986 |
| SU | 1443873 | 12/1988 |
| WO | WO-96/06567 | 3/1996 |
| WO | WO-97/13465 | 4/1997 |
| WO | WO-98/34545 | 8/1998 |
| WO | WO-00/74594 | 12/2000 |
| WO | WO-02/26108 | 4/2002 |

OTHER PUBLICATIONS

J. Kersey The gauze hammock sling operation in the treatment of stress incontinence. British Jour. of Obstet. and Gynec. 90:945-949 (1983).

Bayer et al. A New Approach to Primary Strengthening of Colostomy with Marlex Mesh to Prevent Paracolostomy Hernia. Surgery, Gynecology & Obstretics. 163:579-80 (1986).

Delorme, E. La bandelette trans-obturatrice: un procede mini-invasif pour traiter l'incontinence urinaire d'effort de la femme. Progres en Urologie. 11:1306-13 (2001) (English translation provided).

Giesy et al. Ureteral Instrumentation: A New System for Continued Access Via a Safety Guidewire. Journal of Urology. No. 4, Part 2, p. 282A (1988).

Gittes et al. No-Incision Pubovaginal Suspension for Stress Incontinence. Journal of Urology, 138:3, 568-70 (1987).

Haab et al. Feasibility of Outpatient Percutaneous Bladder Neck Suspension Under Local Anesthesia. Urology. 50:4, 585-897 (1997).

Jacquetin, B. Utilisation du TVT dans la chirurgie de l'incontinence urinaire feminine. J. Gynecol Obstet Biol Reprod. 29, 242-47 (2000).

Kovac et al. Pubic Bone Suburethral Stabilization Sling for Recurrent Urinary Incontinence. Obstetrics & Gynecology, 89:4, 624-27 (1997).

Norris et al. Use of Synthetic Material in Sling Surgery: A Minimally Invasive Approach. Journal of Endourology. 10:3, 227-30 (1996).

Petros et al. An Integral Theory and Its Method for the Diagnosis and Management of Female Urinary Incontinence, Scandinavian Journal of Urology and Nephrology. Supplement 153, 1-93 (1993).

Petros et al. Urethral Pressure Increase on Effort Originates from Within the Urethra, and Continence From Musculovaginal Closure. Neurourology and Urodynamics. 14:4, 337-50 (1995).

Petros, P. Ambulatory surgery for urinary incontinence and vaginal prolapse. Medical Journal of Australia. 161:171-72 (1994).

Petros, P. An Integral Theory of Bladder Neck Opening, Closure and Urinary incontinence in the Female. International Journal of Gynecology & Obstetrics. XXIII World Congress of Gynaecology and Obstetrics (FIGO) 1991.

Petros, P. Medium-term Follow-up of the Intravaginal Slingplasty Operation Indicates Minimal Deterioration of Urinary Continence with Time. Aust NZ J Obstet Gynaecol. 39:3, 354-56 (1999).

Petros, P. The Intravaginal Slingpasty Operation, a Minimally Invasive Technique for Cure of Urinary Incontinence in the Female. Aust. NZ J Obstet Gynaecol. 36:4, 453-61 (1996).

Raz et al. Fascial Sling to Correct Male Neurogenic Sphincter Incompetence: The McGuire/Raz Approach. Journal of Urology. 139:528-31 (1988).

Raz et al. Vaginal Wall Sling. The Journal of Urology. 141:43-6 (1989).

Raz, S. Modified Bladder Neck Suspension for Female Stress Incontinence, Urology. 17:1, 82-5 (1981).

Stamey, T.A. Endoscopic Suspension of the Vesical Neck for Urinary Incontinence in Females. Annals of Surgery. 192:4, 465-71 (1980).

Stamey, T.A. Endoscopic Suspension of the Vesical Neck for Urinary Incontinence. Surgery, Gynecology & Obstetrics. 136:4, 547-54 (1973).

Stamey, T.A. Endoscopic Suspension of the Vesical Neck. Stanton, Tanagho (eds.). Surgery of Female Incontinence. Springer-Verlag, Berlin: 115-32 (1986).

Staskin et al. The Gore-tex sling procedure for female sphincteric incontinence: indications, technique, and results. World J of Urol. 15:5, 295-99 (1997).

Staskin, D.R. Sling Surgery for the Treatment of Female Stress Incontinence. 5:1, 106-22 (1991).

Sussman, et al. The Raz Bladder Neck Suspension: Five-Year Experience. The Journal of Urology. 145, 223A (1993).

Ulmsten et al. A Three-Year Follow Up of Tension Fee Vaginal Tape for Surgical Treatment of Female Stress Urinary Incontinence. British Journal of Obstetrics and Gynaecology. 106, 345-50 (1999).

Ulmsten et al. An Ambulatory Surgical Procedure Under Local Anesthesia for Treatment of Female Urinary Incontinence. The International Urogynecology Journal. 7:81-86 (1996).

Ulmsten et al. Intravaginal Slingplasty (IVS): An Ambulatory Surgical Procedure for Treatment of Female Urinary Incontinence. Scand J Urol Nephrol 29:1, 75-82 (1995).

Ulmsten et al. Intravaginal slingplasty. Zentralbl Gynakol. 116, 398-404 (1994).

Ulmsten et al. Surgery for female urinary incontinence. Current Opinion in Obstetrics & Gynecology. 4:3, 456-62 (1992).

Ulmsten et al. Connective Tissue Factors in the Aetiology of Female Pelvic Disorders. Ann. Med. 22:6, 3 (1990).

Ulmsten, U. An Introduction to Tension-Free Vaginal Tape (TVT)—A New Surgical Procedure for Treatment of Female Urinary Incontinence. Int Urogynecol J. (Suppl 2): S3-4 (2001).

Ulmsten, U. The basic understanding and clinical results of tension-free vaginal tape for stress urinary incontinence. Der Urologe [A] 40:269-73 (2001).

* cited by examiner

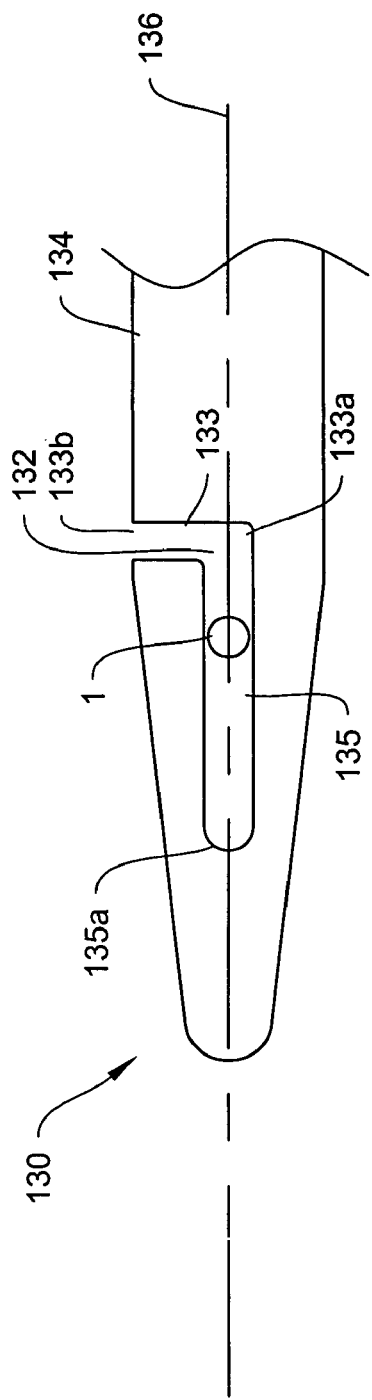
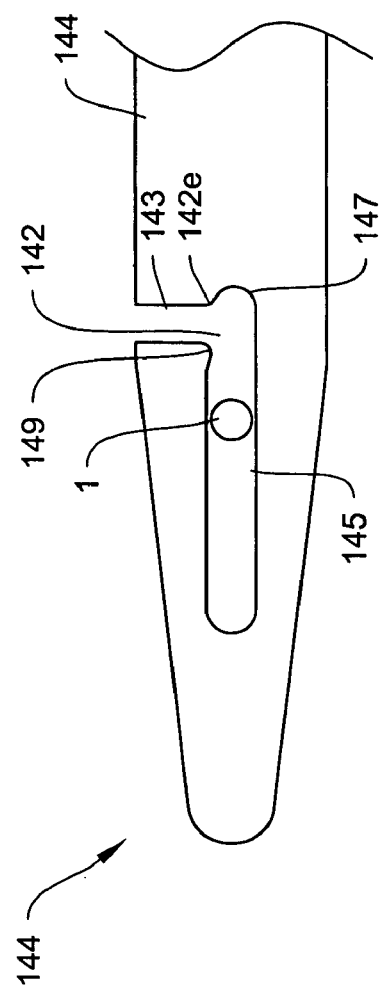
FIG. 13
FIG. 14

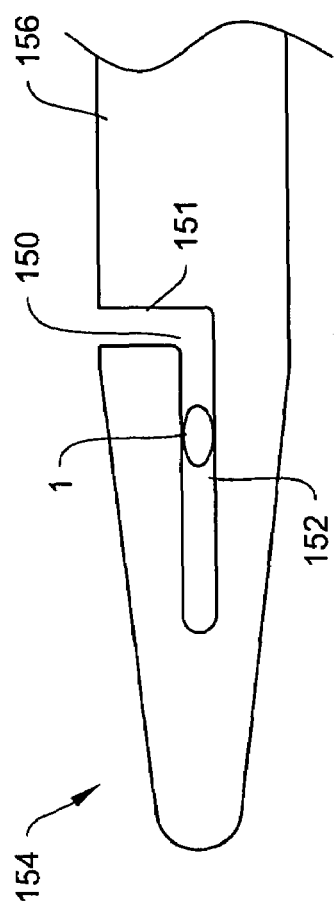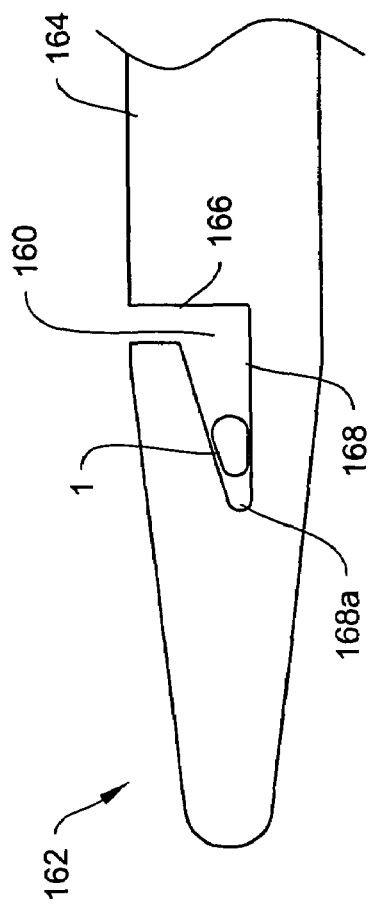

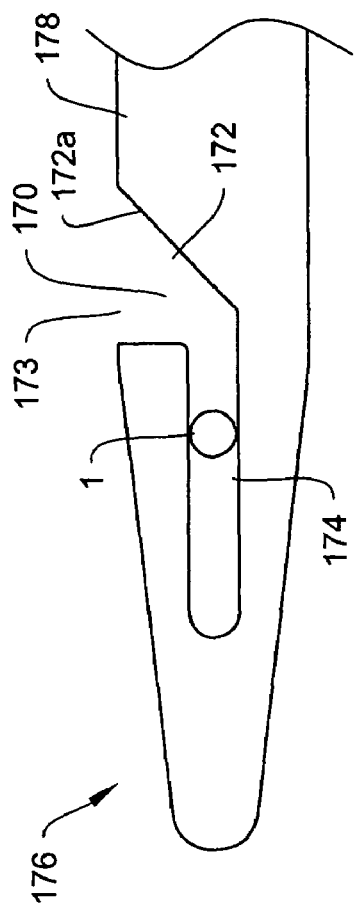
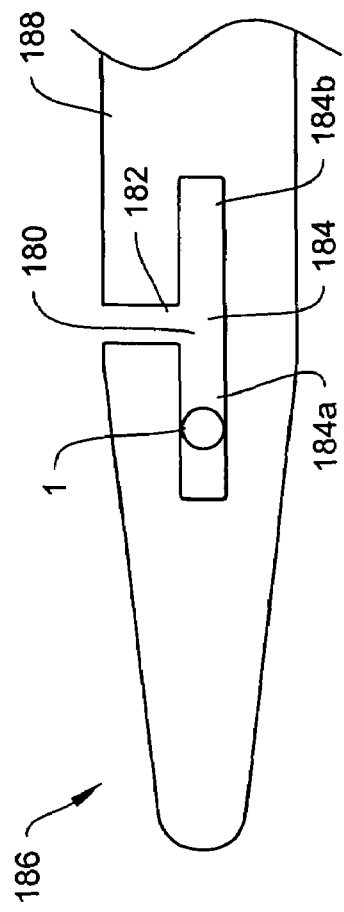

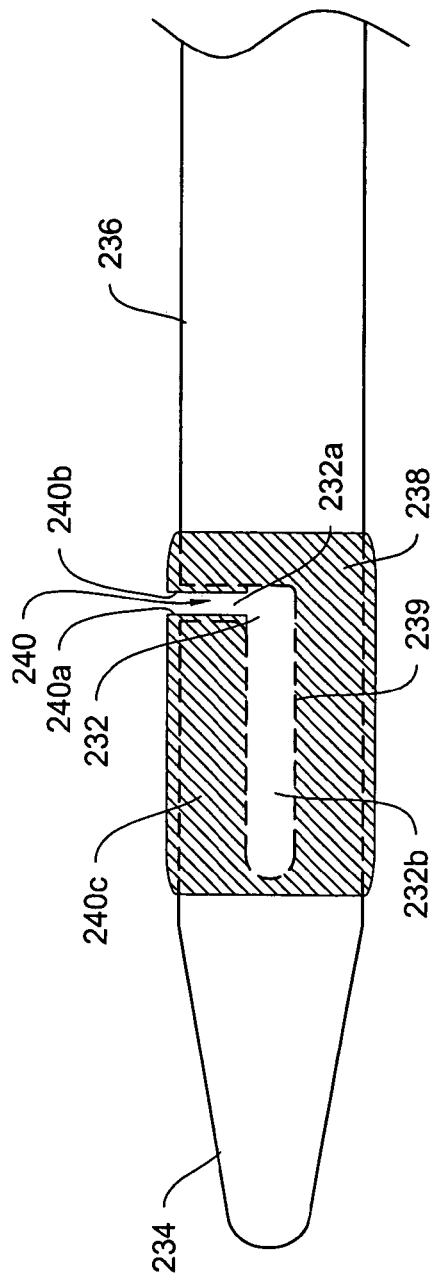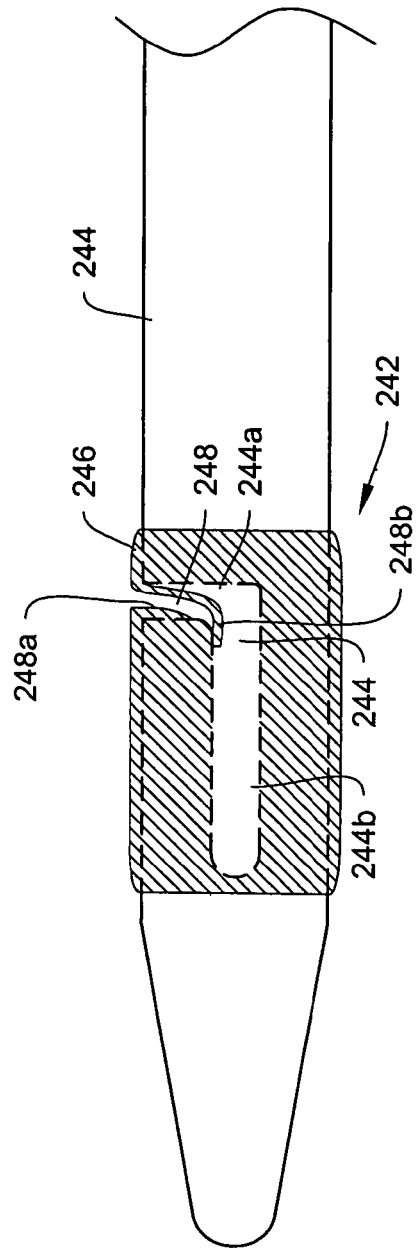
FIG. 21
FIG. 22

SYSTEMS AND METHODS RELATING TO ASSOCIATING A MEDICAL IMPLANT WITH A DELIVERY DEVICE

CROSS-REFERENCE TO RELATED APPLICATIONS

This application claims the benefit of U.S. Provisional Application No. 60/523,208 filed Nov. 17, 2003, the entire disclosure of which is incorporated herein by reference.

FIELD OF THE INVENTION

The invention relates generally to structures located on medical implants and/or on implant delivery devices for associating the medical implant with the delivery device.

BACKGROUND OF THE INVENTION

Urinary incontinence occurs in both men and women. Various types of incontinence are caused by different conditions and call for different treatments. For example, stress urinary incontinence (SUI) is known to be caused by at least two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (for example, due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop. One disadvantage of conventional medical implant systems is that they typically require attaching the implant to a delivery device of some sort. In some instances the making and/or breaking the interconnection requires significant mechanical force, which can be both inconvenient for a medical operator and can risk damage to patient tissue near the implantation site.

Accordingly, there is a need for an improved approach to associating a medical implant, such as a sling assembly, with a delivery device.

SUMMARY OF THE INVENTION

The invention relates to cooperating structures for associating a medical implant with a delivery device or assembly (collectively a "delivery device"). According to a preferred embodiment, the medical implant includes an implantable sling and the delivery device is a device for delivering the implantable sling to an anatomical location in the body of a patient. Preferably, the sling is configured for midurethral placement for treating urinary incontinence. In some embodiments, the sling resides, at least partially, in a protective sheath, and is part of a sling assembly. According to various embodiments, a structure located on an end of the sling assembly cooperates with a mating structure on a distal portion of a delivery device shaft to associate the sling assembly with the delivery device. According to one aspect, the structure located on the sling assembly includes an association loop.

According to one embodiment, the association loop attaches to a dilator, also located at the end of the sling assembly. In one preferred configuration, the sling assembly includes a dilator at each end, with an association loop extending out of an end of each dilator. The association loops may be oriented, for example, in substantially the same plane as a sling included in the sling assembly, or in a plane substantially orthogonal to the plane of the sling. The association loop may be formed from a substantially rigid material or may be formed from a deformable material. Preferably, the association loop is formed from a deformable, yet generally resilient, shape-retaining material. However, in some configurations, the association loop is formed from a non-shape-retaining, suture-like material. According to a further embodiment, a filament is embedded and secured along the length of a dilator, and extends from a conical tip of the dilator to form an association loop. In one configuration, the dilator has an axially extending channel, and the filament ends are affixed in the axially extending channel by crimping them within a crimp tube. In other configurations, the dilator includes a biasing member, such as a spring, interfitted with the crimp tube within a cavity of the dilator. According to one feature, pulling on the association loop compresses the spring and extends more of the loop filament out of the dilator to effectively increase the size of the association loop. When the pulling ceases, the spring decompresses to retract a portion of the loop filament into the dilator and effectively reducing the size of the association loop. The bias spring may also be configured to enable the association loop to rotate relative to the dilator to allow the medical operator to twist or untwist the sling while the loop is coupled to the delivery device. The loop may include features, such as one or more bends, to maintain the loop external to the dilator.

In an alternative embodiment, a portion of the association loop external but near to the dilator may be twisted to effectively reduce the size of the association loop. The twisted section may also be employed to position an open portion of the association loop a desired reference distance from the dilator. In another embodiment, the association loop is placed a desired reference distance from the dilator by placing a tube of a desired length between the dilator and the loop. The tube may be separate from or part of the dilator.

The association loop may be formed from a single or multi-stranded filament. Multiple strands of material may be twisted together to form a flexible and/or resilient loop filament. In another embodiment, the multiple strands may be woven together to form a braided filament. Alternatively, the multiple strands may be woven to form a tube-shaped filament having an inner and outer diameter. An association loop formed from a braided tube may change shape when a force is applied. For example, in response to pulling on the association loop, its length may increase while the inner and outer diameters of the filament decrease. In other embodiments, the loop may be coated with a polymer.

In one aspect of the invention, the structure located in the distal portion of the delivery device shaft includes an L- or T-shaped slot. In one configuration, an a L-slot is formed as a first section extending radially into the distal portion of the delivery device shaft, and a second section extending from an inner end of the first section axially in a distal direction along the delivery device shaft. In alternative embodiments, the second section of the L-slot extends axially in a proximal direction. The slot may include additional structures, such as indentations, protuberances, coatings, and/or flaps for impeding, but not prohibiting, the association loop from disassociating with the L-slot. Additionally, the radially extending first section may have the same or different dimensions as the axially extending second section. The radially and axially extending sections may have constant or varying widths. For example, the radially extending section may taper inward from the radial opening on the delivery device shaft to its inner terminal end.

In another embodiment, the delivery device shaft may include a sheath for partially or substantially surrounding the axial opening to the L-slot. The sheath may partially extend over the axial opening L-slot or form a flap overhanging the axial opening to impede an association loop from unhooking/disassociating from the L-slot.

Any delivery device may be modified to include an association structure as described above. For example, any delivery device configured for suprapubic, pre-pubic, transvaginal, or transobtural delivery of an implant may employ an association structure of the invention.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting in any way.

FIG. 13 shows an L-slot formed in a distal portion of a delivery device shaft according to an illustrative embodiment of the invention.

FIG. 14 shows an L-slot formed in a distal portion of a delivery device shaft and including an indentation and a protuberance for facilitating retention of an association loop according to an illustrative embodiment of the invention.

FIG. 15 shows an L-slot formed in a distal portion of a delivery device shaft wherein a radially extending leg of the L-slot is wider than an axially extending leg for facilitating ease of insertion into the radially extending leg and for facilitating retention of an association loop in the axially extending leg according to another illustrative embodiment of the invention.

FIG. 16 shows an L-slot formed in a distal portion of a delivery device and having a tapered axially extending leg for facilitating retention of an association loop in that leg according to another illustrative embodiment of the invention.

FIG. 17 shows another illustrative L-slot formed in a distal portion of a delivery device wherein the radially extending leg has a tapered shape for facilitating insertion of an association loop, and the axially extending leg has a narrowed width to facilitate retention of the association loop according to another illustrative embodiment of the invention.

FIG. 18 shows a T-shaped structure formed in a distal portion of a delivery device for engaging with an association loop according to another illustrative embodiment.

FIG. 21 shows the L-slot structure of FIG. 13 including another illustrative embodiment of a sheath that partially surrounds the L-slot structure.

FIG. 22 shows the L-slot structure of FIG. 13 including another illustrative embodiment of a sheath that includes a flap portion that extends into the radially extending leg of the L-slot.

ILLUSTRATIVE DESCRIPTION

Figure 1:
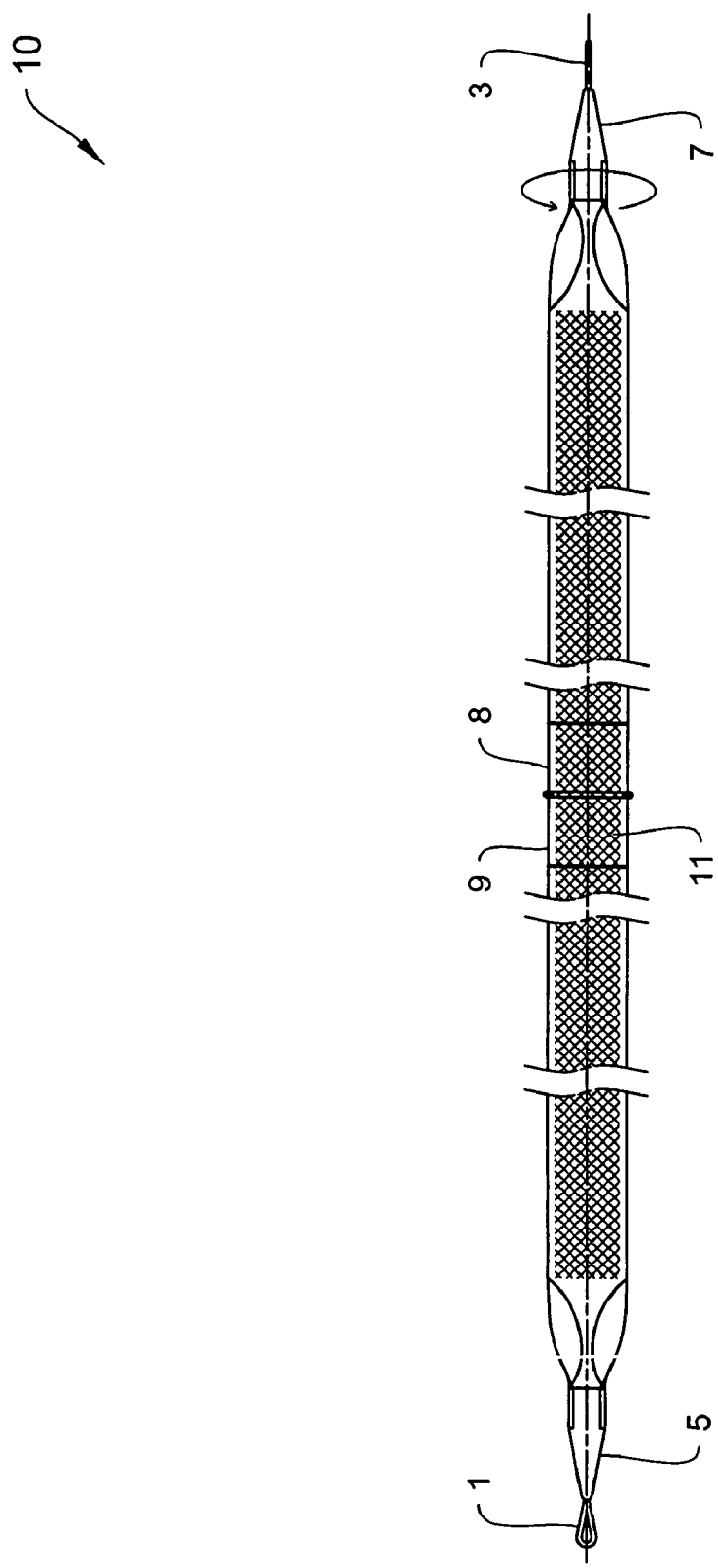
FIG. 1 depicts a sling assembly including association loops according to an illustrative embodiment of the invention.

The invention relates to cooperating structures on one or more ends of a medical implant assembly and on an end of a delivery device to enable a medical operator to associate the medical implant assembly with the delivery device so that the medical operator may deliver the implant to an anatomical location in a patient's body. Preferably, the implant assembly is a sling assembly including a sling for treating urinary incontinence, and the anatomical site is in the periurethral tissue of the patient (e.g. under a bladder neck or mid-urethral location).

Without limitation, examples of features of various sling configurations that may be employed with illustrative embodiments of the invention are disclosed in U.S. Ser. No. 10/092,872, entitled "Medical slings," U.S. Ser. No. 10/640, 838, entitled "Medical implant," U.S. Ser. No. 10/641,170, entitled "Medical slings," U.S. Ser. No. 10/641,192, entitled "Medical slings," U.S. Ser. No. 10/918,123, entitled "Surgical Slings," the entire contents of all of which are incorporated herein by reference.

Additionally, examples of features of various delivery systems that may be employed with illustrative embodiments of the invention include, without limitation, those delivery systems configured for supra-pubic, pre-pubic, transvaginal, and/or transobtural procedures. Again, without limitation, examples of features of dilators, slings, sling assemblies, delivery devices and implantation approaches that may be employed with illustrative embodiments of the invention are disclosed in U.S. Pat. No. 6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," U.S. Ser. No. 10/015,114, entitled "Devices for minimally invasive pelvic surgery," U.S. Ser. No. 10/774,826, entitled "Devices for minimally invasive pelvic surgery," U.S. Ser. No. 10/093,398, entitled "System for implanting an implant and method thereof," U.S. Ser. No. 10/093,498, entitled "System for implanting an implant and method thereof," U.S. Ser. No. 10/093,371, entitled "System for implanting an implant and method thereof," U.S. Ser. No. 10/093,424, entitled "System for implanting an implant and method thereof," U.S. Ser. No. 10/093,450, entitled "System for implanting an implant and method thereof," U.S. Ser. No. 10/094,352, entitled "System for implanting an implant and method thereof," U.S. Ser. No. 10/631,364, entitled "Bioabsorbable casing for surgical sling assembly," U.S. Ser. No. 10/641,376, entitled "Spacer for sling delivery system," U.S. Ser. No. 10/641,487, entitled "Systems, methods and devices relating to delivery of medical implants," U.S. Ser. No. 10/642,395, entitled "Systems, methods and devices relating to delivery of medical implants," U.S. Ser. No. 10/642,397, entitled "Systems, methods and devices relating to delivery of medical implants," U.S. patent application Ser. No. 10/642, 365, entitled "Systems, methods and devices relating to delivery of medical implants," U.S. Ser. No. 10/832,653, entitled "Systems and methods for sling delivery and placement," U.S. patent application Ser. No. 10/939,191, entitled "Devices for minimally invasive pelvic surgery," U.S. patent application Ser. No. 10/957,926, entitled "Systems and methods for delivering a medical implant to an anatomical location in a patient," U.S. Provisional Application No. 60/569,300, entitled "Systems and methods for delivering a medical implant to an anatomical location in a patient," and U.S. Provisional Application No. 60/508,600 entitled "Systems and methods for delivering a medical implant to an anatomical location in a patient," the entire contents of all of which are incorporated herein by reference.

FIG. 1 depicts a sling assembly 10, which includes an association loop 1 attached via a dilator 5 to an end of a sleeve 9 holding an implantable sling 11. Another association loop 3 attaches via a dilator 7 to the other end of the sleeve 9. The association loop 1 is shown as substantially in the plane of the sleeve 9. It is to be understood that the association loop 1 may be configured at other angles relative to the plane of the sleeve 9. For example, the associate loop 3 may be in a plane substantially orthogonal to the plane of the sleeve 9. Furthermore, the association loops 1 and 3 may be substantially in the same plane or in different planes. In certain embodiments, the association loops 1 and 3 may be fixed at a specific angle relative to the plane of the sleeve 9, for example, in a plane about 30, 45, 60 or 90 degrees to the plane of the sleeve 9. In other embodiments, the association loops 1 and 3 may be configured to rotate 360 degrees relative to the plane of the sleeve 9.

In alternative embodiments, the association loop 1 can be configured into any shape that allows it to cooperate with a complementary structure located on a delivery device. For example, the association loop 1 can have an irregular shape or it can be, for example, substantially circular, teardrop, triangular, square, rectangular or a combination of these shapes. In one example, the association loop 1 is open, for example, forms a hook or forms an eyelet. In another example, the loop is closed. The loop can be resilient, rigid, semi-rigid, and/or flexible. Preferably, the loop is flexible enough to deform as it is pushed/pulled through tissue, but rigid enough to maintain its integrity (i.e., not break) against the pushing/pulling force. The association loop 1 can be made from any suitable material, such as a wire or a suturing material. Preferably the loop is made of a biocompatible material that allows for the resiliency, flexibility and rigidity described above, for example, metal, plastic, polymers, etc.

The association loop 1 can also be of any suitable size, for example, the association loop 1 can have a diameter that is just large enough to slide over an end of a delivery device or a delivery needle. The association loop 1, when it is configured to have such a diameter, helps to maintain the cooperation between the association loop 1 and the delivery device during placement of the sling. The association loop 1 may also be sized to be long enough such that when hooked on to a complementary structure near a distal end of a delivery device and pulled by a user with enough force away from the distal tip of a delivery device, the association loop 1 swings about the tip of the delivery device for removal.

The association loop can be formed from a single stranded filament or can be formed from a multi-stranded filament. The multiple strands may be braided or twisted together. The use of multiple strands to form the association loop 1 is preferred because a multi-stranded loop may provided more structural flexibility than an association loop formed from a single strand.

Any suitable adaptor may be used to attach the association loop 1 with a particular medical implant assembly. For example, in FIG. 1, the sling assembly 10 employs the dilators 5 and 7 for attaching the association loops 1 and 3, respectively, to the ends of the plastic sleeve 9. More specifically, the knitted mesh 11 resides, at least partially, within the plastic sleeve 9. An opening 8, located at a midpoint of a top portion of the plastic sleeve 9, exposes the entire width of the knitted mesh 11. The knitted mesh 11 may be made entirely of polypropylene, may be approximately 1 cm in width and 45 cm in length, and terminates at free ends. The knitted mesh 11, including both free ends, does not connect to the plastic sleeve 9 or anything else. This feature enables a medical operator to pull on the ends of the plastic sleeve 9 during sling placement, for example, via the dilators 5 and 7, the association loops 1 and 3, and/or the delivery devices, without risk of stretching, curling or otherwise deforming the knitted mesh 11.

A tabbed spacer (not shown) is located at a midpoint of a bottom side of the plastic sleeve 9, and encloses a looped portion of the bottom side of the plastic sleeve 9. The tabbed spacer can be used during implantation as a visual aid to placement of the implant assembly. The tabbed spacer also engages the looped portion of the bottom side of the plastic sleeve 9 and prohibits the plastic sleeve 9 from sliding off, or otherwise being removed from, the knitted mesh 11 during implant assembly placement. The tabbed spacer must be cut to enable the plastic sleeve 9 to slide off the knitted mesh 11. This feature ensures that the plastic sleeve 9 cannot be removed simply by applying a pulling force, such as that applied to the implant assembly ends by a medical operator during implant assembly placement. After the sling assembly 10 is positioned within the patient, a cut is made through the center of the tabbed spacer, and thus through the looped portion of the bottom side of the plastic sleeve 9. The plastic sleeve 9 is then slid off of the knitted mesh 11, out of the body of the patient, and discarded, along with the dilators 5 and 7.

Figure 2:
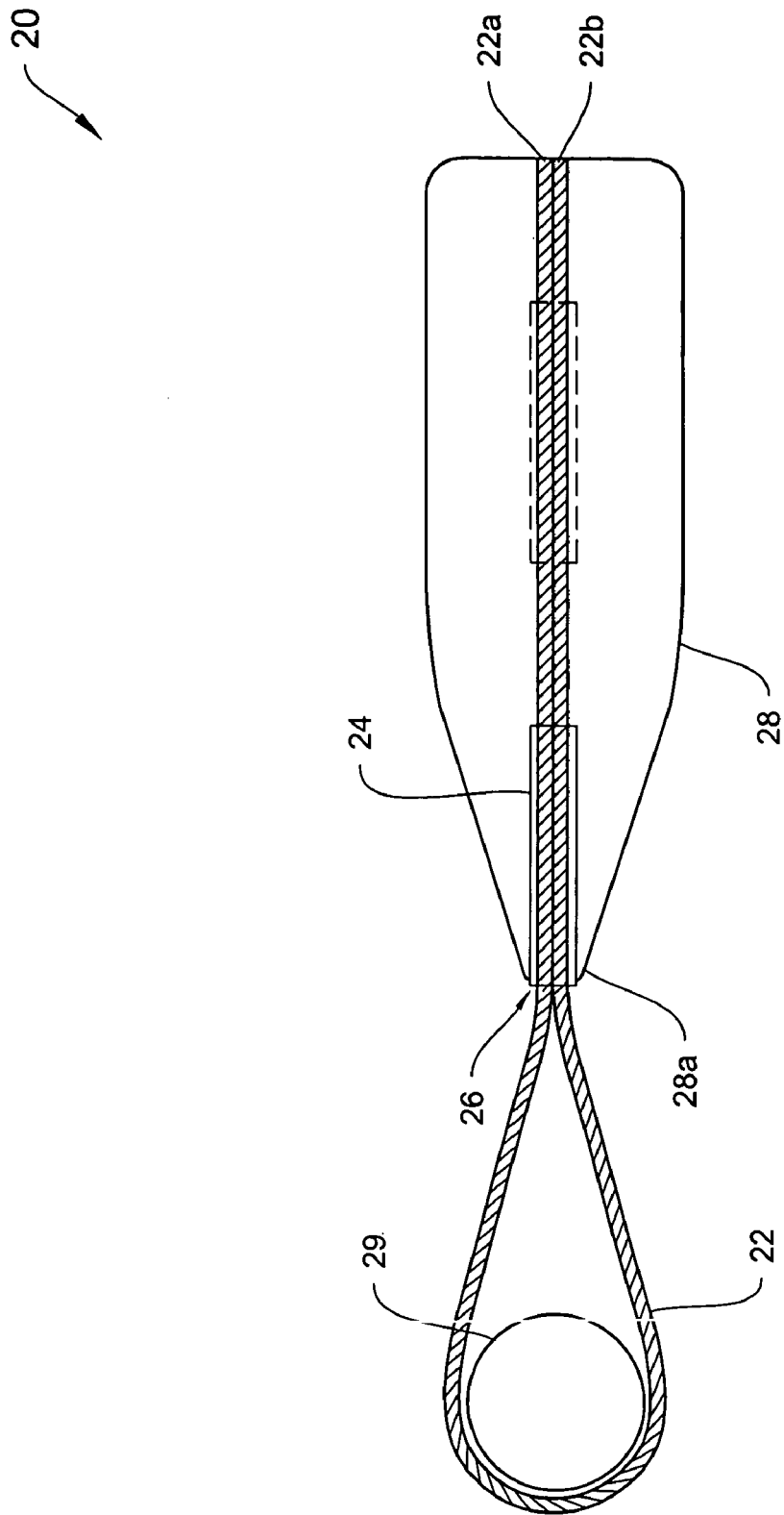
FIG. 2 depicts an association loop affixed into a dilator assembly according to an illustrative embodiment of the invention.

FIG. 2 depicts dilator assembly 20 including an association loop 22 according to an illustrative embodiment of the invention. In this embodiment, the association loop 22 is formed from a multi-stranded twisted filament. A pin 29 is used to size and shape the association loop 22. The filament ends 22a and 22b are inserted through an axially extending channel 26 into a crimp tube 24. A second crimp tube is depicted in outline to demonstrate that the crimp tube 24 may be placed at any location along the filament ends 22a and 22b. The crimp tube 24, once compressed (i.e., crimped), serves to lock the filament ends 22a and 22b together to form the loop 22. The filament ends 22a and 22b, including the crimp tube 24 may affixed into the dilator 28 in any suitable manner. For example, the dilator 28 may be injection molded around the filament ends 22a and 22b, and/or the crimp tube 24. The filament ends 22a and 22b and the crimp tube 24 can be permanently or removably positioned within the dilator 28. For example, the filament ends 22a and 22b may be permanently attached to the dilator 28 by, for example, molding or gluing the dilator 28 over the filament ends 22a and 22b and the crimp tube 24.

In this embodiment, the loop ends 22a and 22b are shown to be entirely inside the dilator 28 and a portion of the crimp tube 24 is located external to the dilator 28. As depicted in FIG. 2, the loop 22 extends from the tapered end 28a of the dilator 28.

In one example, the length of a dilator is preferred to be greater than about 0.3 inches long to aid in passage through a patient's body. However, in other embodiments, it may be less than about 0.3 inches. In other embodiments, the dilator length is between about 0.2 inches and about 10.0 inches. In preferred embodiments, the dilator length is between about 0.3 inches and about 2.0 inches. One advantage of the longer dilators, for example, dilators having a length greater than about 2.0 inches, is that the dilators can be used to untwist the sling assembly before pulling the plastic sleeve and knitted mesh into the body.

A dilator may include a conical portion and a straight portion. The straight portion has a constant diameter. The conical portion has a diameter that varies and decrease from the diameter of the straight portion. Preferably, the diameter of the straight portion of a dilator will be about 0.25 inches. However, the diameter of the straight portion of a dilator may be from about to 0.1 about 0.8 inches.

Figure 3:
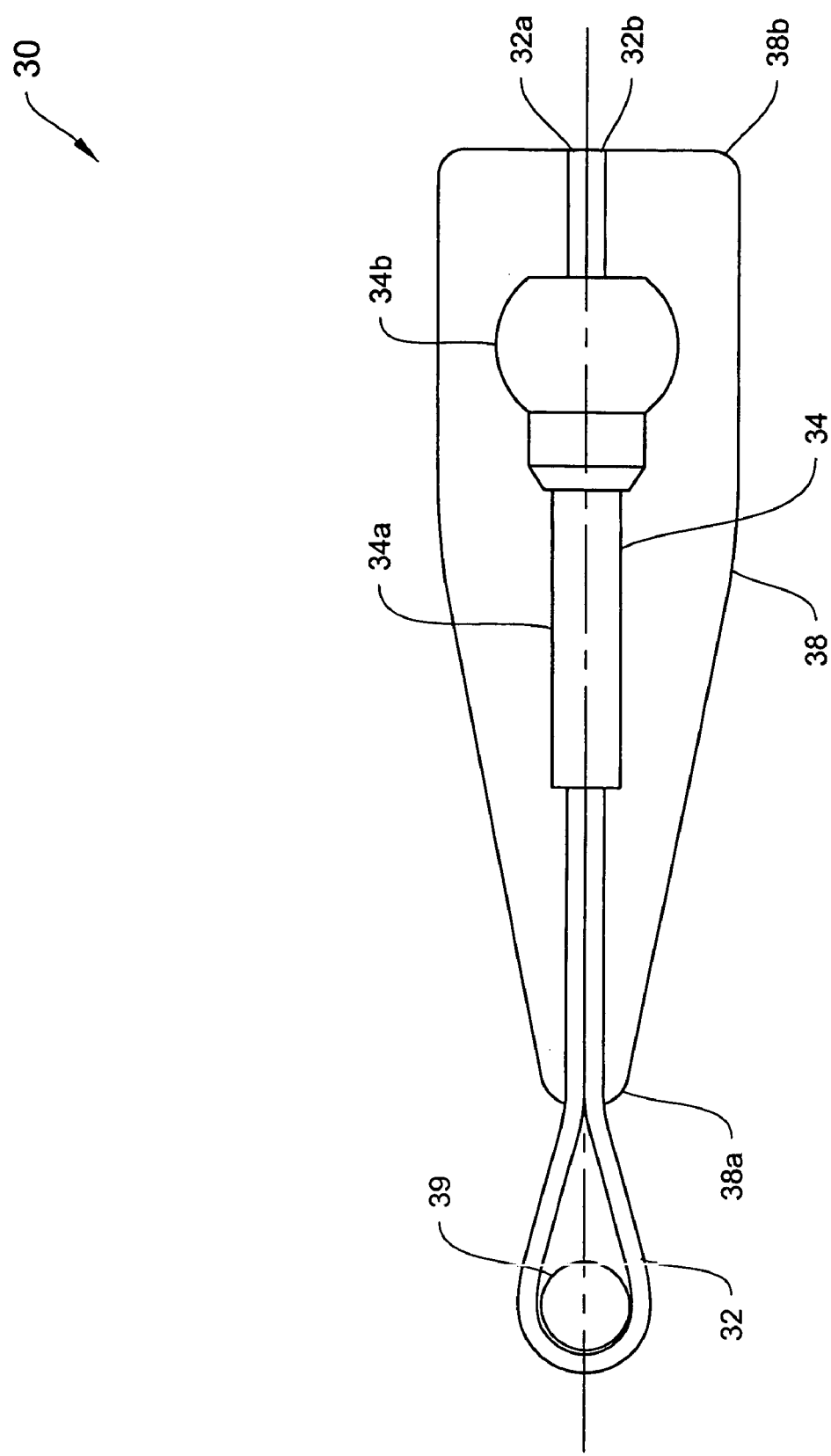
FIG. 3 depicts an association loop affixed into a dilator assembly according to a alternative illustrative embodiment of the invention.

FIG. 3 depicts an alternate embodiment of a dilator assembly 30 including a tissue dilator 38 and an association loop 32 according to another illustrative embodiment of the invention. As in the case of the illustrative embodiment of FIG. 2, the filament ends 32a and 32b of the association loop 32 pass through a crimp tube 34. As an improvement over the FIG. 2 embodiment, the crimp tube 34 includes a ball section 34b and a shank section 34a. The shank section 34a is crimped to ensure filament retention, while the ball section 34b creates further resistance against the association loop 32 being inadvertently pulled out of the dilator 38. The association loop 32 and the crimp tube 34 may be insert-molded into the dilator 38. A pin 39 is used to size and shape the association loop 32.

Figure 4:
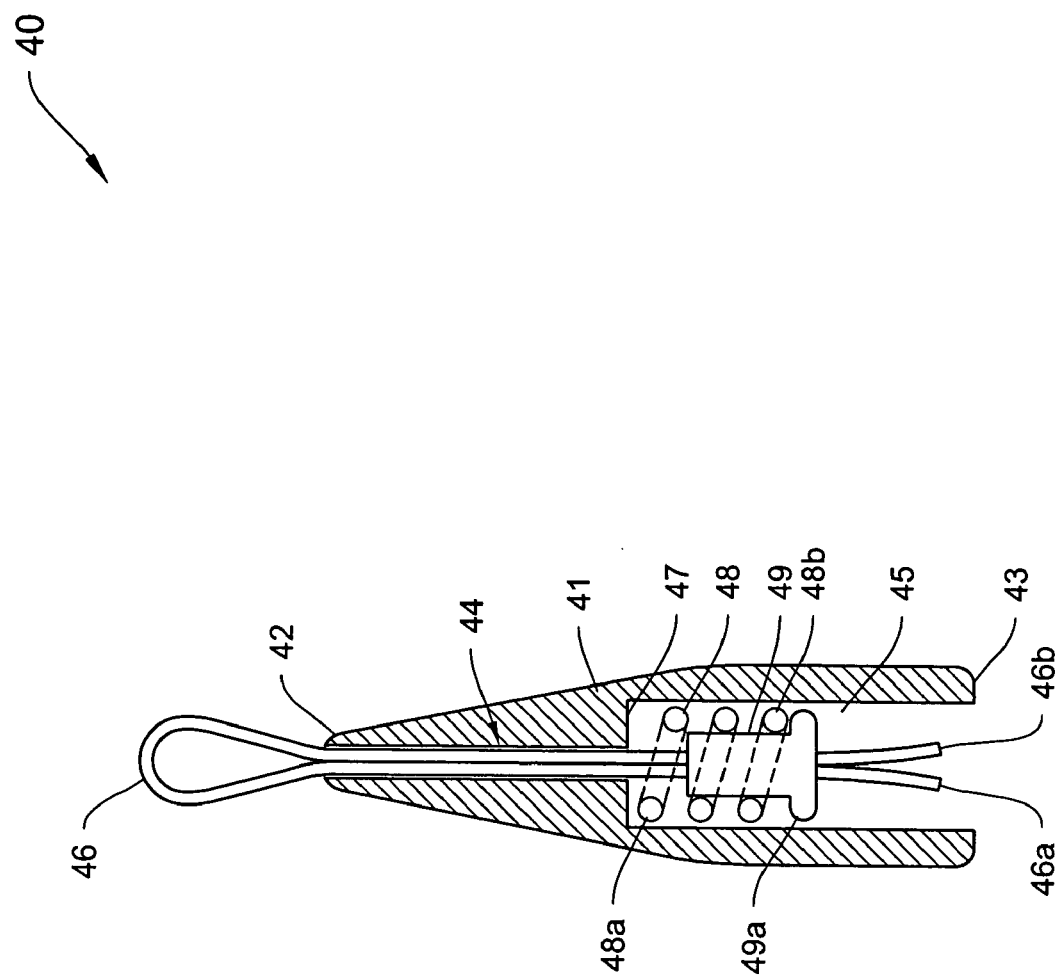
FIG. 4 depicts an association loop having a biasing mechanism and affixed into a dilator assembly according to another alternative illustrative embodiment of the invention.

FIG. 4 shows an alternative illustrative embodiment of a dilator assembly 40 having an extendable association loop 46 according to the invention. The dilator assembly 40 includes a tissue dilator 41 having a leading end 42 and a trailing end 43. The leading end 42 is the end of the dilator that is first inserted into a patient's tissues, and is tapered to increase the size of a tunnel formed initially by a shaft of a delivery device. The increased tunnel size eases the passage of a sling assembly or other medical implant. As in the case of previously disclosed embodiments, an association loop 46 extends out of the leading end 42 of the dilator 41. As depicted, the dilator 41 includes a channel 44 extending axially through the dilator 41 from the leading end 42 to an intermediate shoulder 47, and a channel 45 extending axially through the dilator 41 from the intermediate shoulder 47 to the trailing end 43. The channels 44 and 45 are in fluid communication with each other, with the channel 44 having a reduced diameter relative to the channel 45, and with the reduced diameter being delineated by the intermediate shoulder 47. A biasing element, such as the spring 48, is seated within the channel 45, with a leading end 48a abutting the shoulder 47. As in the case of FIGS. 2 and 3, the association loop 46 is formed from a filament having two terminal ends 46a and 46b. The terminal ends 46a and 46b thread through the channel 44 and the spring 48. A crimp tube 49 interfits over the filament ends 46a and 46b and is crimped for retention. The crimp tube 49 then concentrically interfits into the spring 48. As shown, the crimp tube 49 includes a radially extending rim 49a. The radially extending rim 49a is wider than the inner diameter of the spring 48 and abuts the trailing spring end 48b. FIG. 4 shows the spring 48 in an uncompressed state.

In operation, in response to pulling on the association loop 46, the radially extending rim 49a of the crimp tube 49 engages the trailing end 48b of the spring 48 and causes the spring 48 to compress, also causing an additional length of the filament forming the association loop 46 to extend out of the leading end 42 of the dilator 41. Extending additional filament out of the dilator 41 effectively increases the size of the association loop 46. This type of spring biasing enables the association loop 46 to expand over a particular delivery device feature during association with the delivery device, and then to retract to impede the association loop 46 from becoming disassociated with the delivery device during implantation.

A crimp tube as depicted in FIGS. 2, 3, and 4 may have an outer diameter of about 0.5 mm, 1 mm, or about 2 mm larger than the association loop ends. The crimp tube may have a constant or varying diameter and may include other structural features, such as a shoulder, a ledge, an indent, and/or a slot.

When used in combination with a spring, the crimp tube and spring are sized such that at least a portion of the crimp tube is larger than the inner diameter of the spring to enable the crimp tube to engage and compress the spring in response to a pulling force on the association loop.

Figure 5:
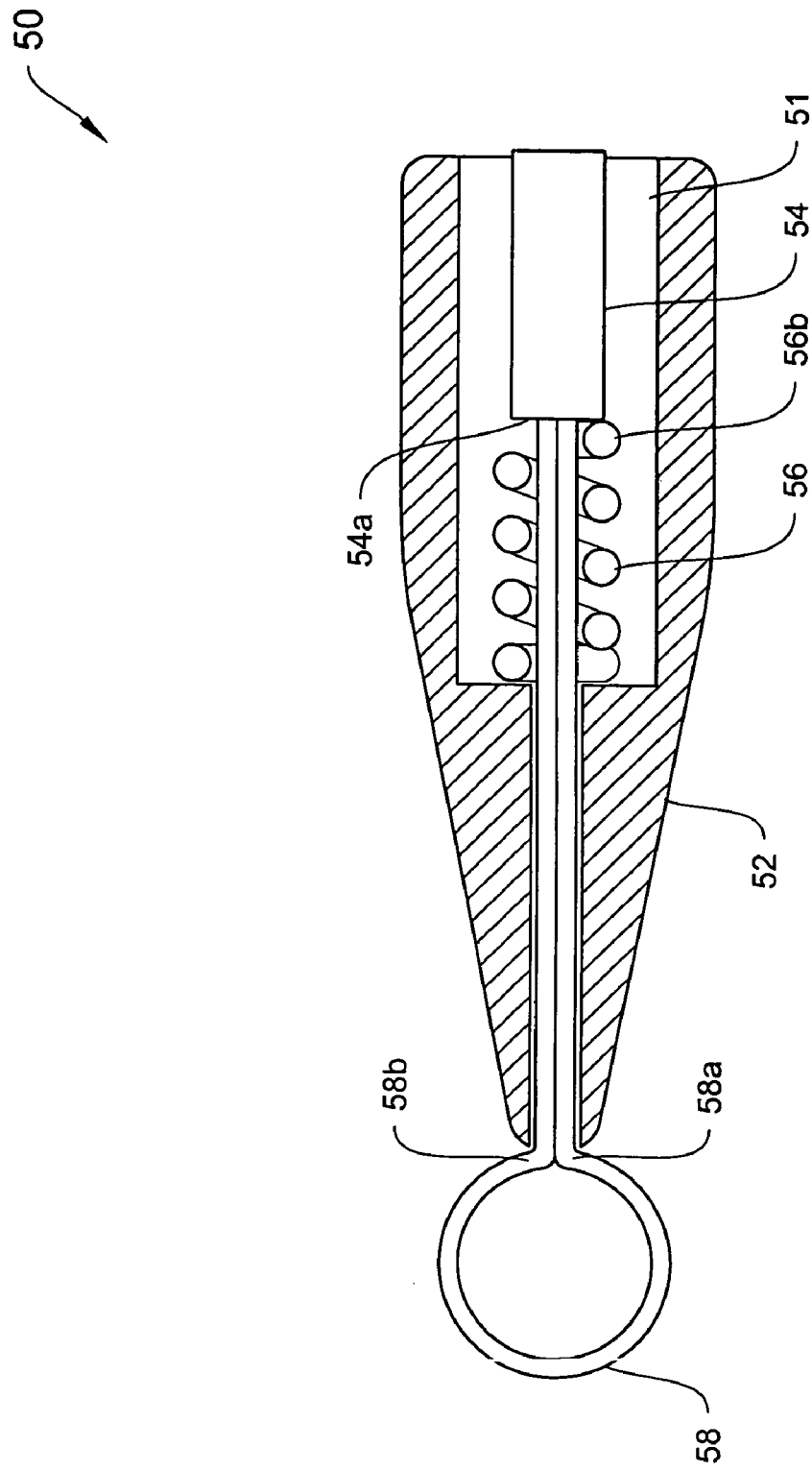
FIG. 5 depicts an association loop having an alternative shape, a biasing mechanism and affixed into a dilator assembly according to another illustrative embodiment of the invention.

FIG. 5 depicts another embodiment of an association loop and dilator assembly 50 including a crimp tube 54, a spring 56, a dilator 52, and an association loop 58 where the association loop 58 include bends 58a and 58b just distal and external to the dilator 52. The dilator assembly 50 operates in a substantially similar fashion to the previously discussed dilator assembly 40, the difference being primarily in the configuration of the crimp tube 54 and the inclusion of bends 58a and 58b in the association loop 58. Rather than engaging the biasing spring 48 with a radially extending rim 49a, the crimp tube 54 has an increased diameter along its entire length. The crimp tube 54 has a diameter wider than the inner diameter of the spring 56 and, thus, enables it to be positioned with its leading end 54a abutting the trailing end 56b of the spring 56. In operation of this embodiment, pulling on the association loop 58 causes the leading end 54a of the crimp tube 54 to engage with the trailing end 56b of the spring 56 also causing the spring 56 to compress. Furthermore, the compression of the spring 56 allows an additional length of loop filament to extend out of the dilator 52. The bends 58a and 58b inhibit the association loop 58 itself from being retracted back into the dilator 52. The bends 58a and 58b may also maintain the spring 56 and the crimp tube 54 within a channel 51 of the dilator 52 during assembly, as the trailing end of the dilator 52 may be left open. In alternative embodiments, the trailing end of the dilator 52 may be closed and the dilator 52 may enclose the crimp tube 54 within the cavity 51. It is to be understood that the configuration of the crimp tube 54 and the spring 56 may be employed in combination with an association loop having any of the various shapes as described herein.

Figure 6:
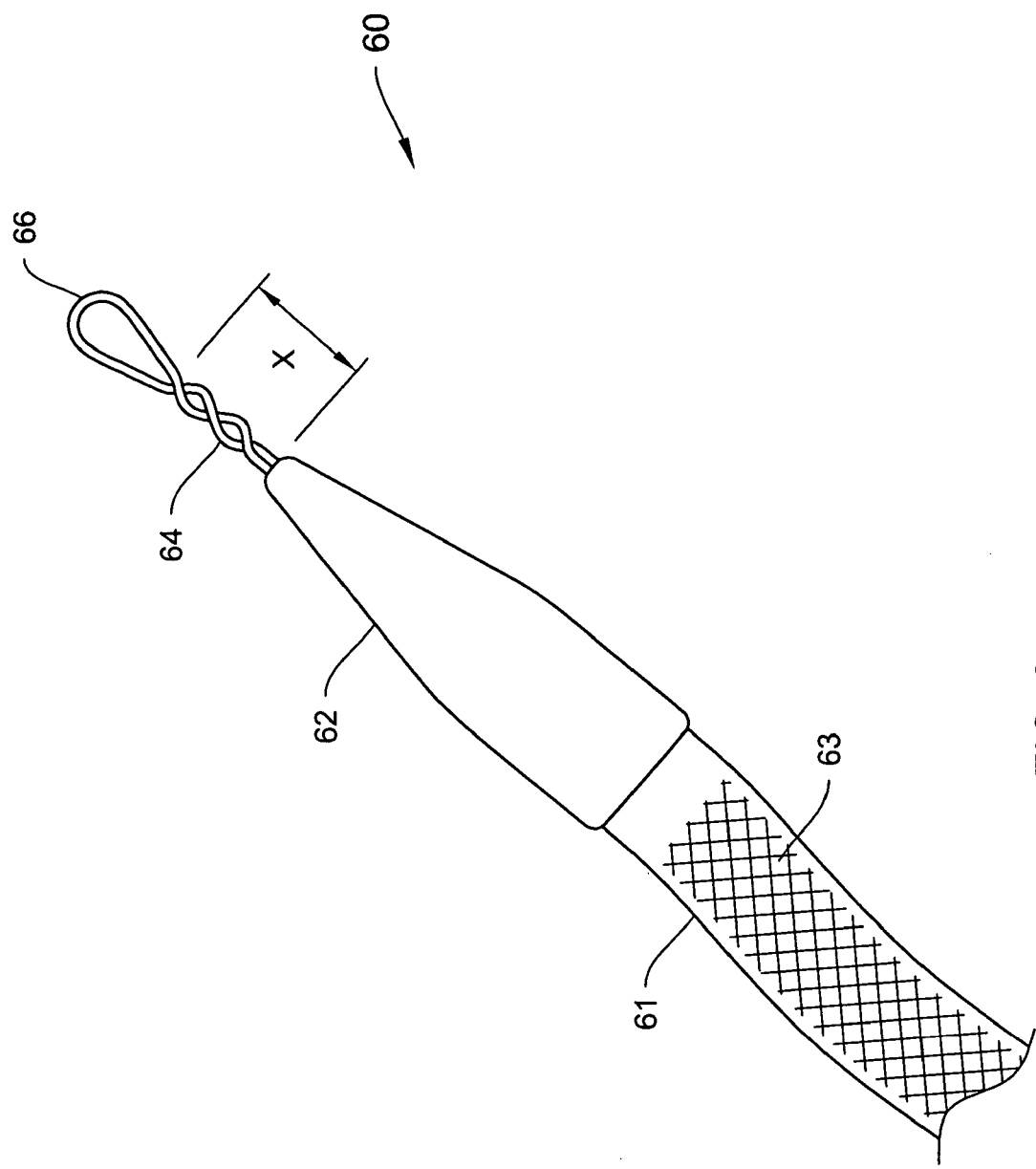
FIG. 6 depicts an association loop having a twisted portion affixed into a dilator assembly connected to an end of a sling assembly according to another illustrative embodiment of the invention.

FIG. 6 depicts another embodiment of a dilator assembly 60. In this embodiment, the filament forming an association loop 66 twists around itself subsequent to extending out of the dilator 62 to form a twisted section 64. The illustrative twisted section 64 has a length X, which may be increased by additional twisting or decreased by reduced twisting. As can be seen, increased twisting also reduces the size of the association loop 66, while reduced twisting increases the size of the association loop 66. Additionally, the twisting can be used to change the orientation of the association loop 66 relative to the orientation of the sleeve 61 and the sling 63 contained within the sleeve 61. The twisted section 64 of distance X can be bent to position the dilator 62 in front of a shaft tip of a delivery device to provide a smooth pull-through due to the inline profile of the shaft and dilator. This embodiment provides an easily used mechanism for forming an association loop 66 having a predetermined size and a predetermined distance X from the leading end of the dilator 62. The twisted section 64 may add a distance X between the sleeve 61 and the association loop 66, without the need for changing the length of the dilator 62.

Figure 7:
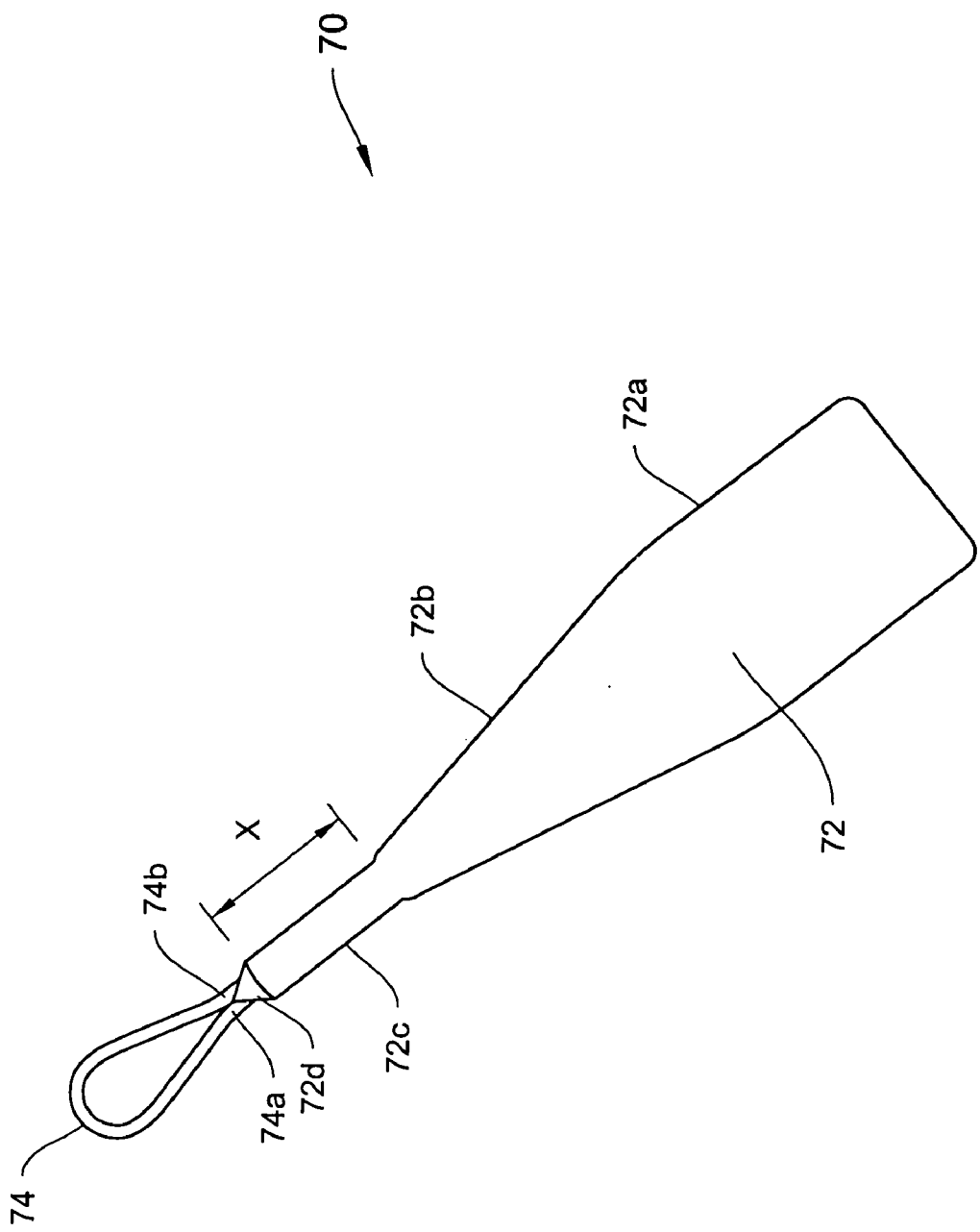
FIG. 7 depicts an association loop affixed in a dilator assembly and including an extension portion for positioning the association loop a desired distance away from the tissue dilating portion of the dilator assembly according to another illustrative embodiment of the invention.

FIG. 7 depicts another illustrative embodiment of an association loop 74 formed into a dilator 72. In this embodiment, the dilator 72 has three sections, a trailing section 72a, an intermediate conical section 72b, and a leading section 72c. The intermediate conical section 72b extends from the trailing section 72a. The leading section 72c terminates in a conical tip 72d and extends from the intermediate section 72b. The association loop 74 extends from the conical tip 72d of the leading section 72c much in the same way as the association loop 66 extends from the dilator 62 in FIG. 6. One function of the leading section 72c is to space the association loop 74a distance X from the end of the intermediate conical section 72b, without the need for any filament twisting.

In the depicted embodiment, the filament ends 74a and 74b are embedded in the dilator 72 in any suitable fashion, including any of those described herein. In some configurations, the leading section 72c may be substantially hollow or solid, and may be substantially rigid or deformable. In some configurations, the leading section 72c may be formed integral with the intermediate section 72b or may be a separate component that interfits over the association loop 74 to adjust the size of the association loop 74 and/or space it a distance X from the end of the intermediate section 72b.

Figure 8:
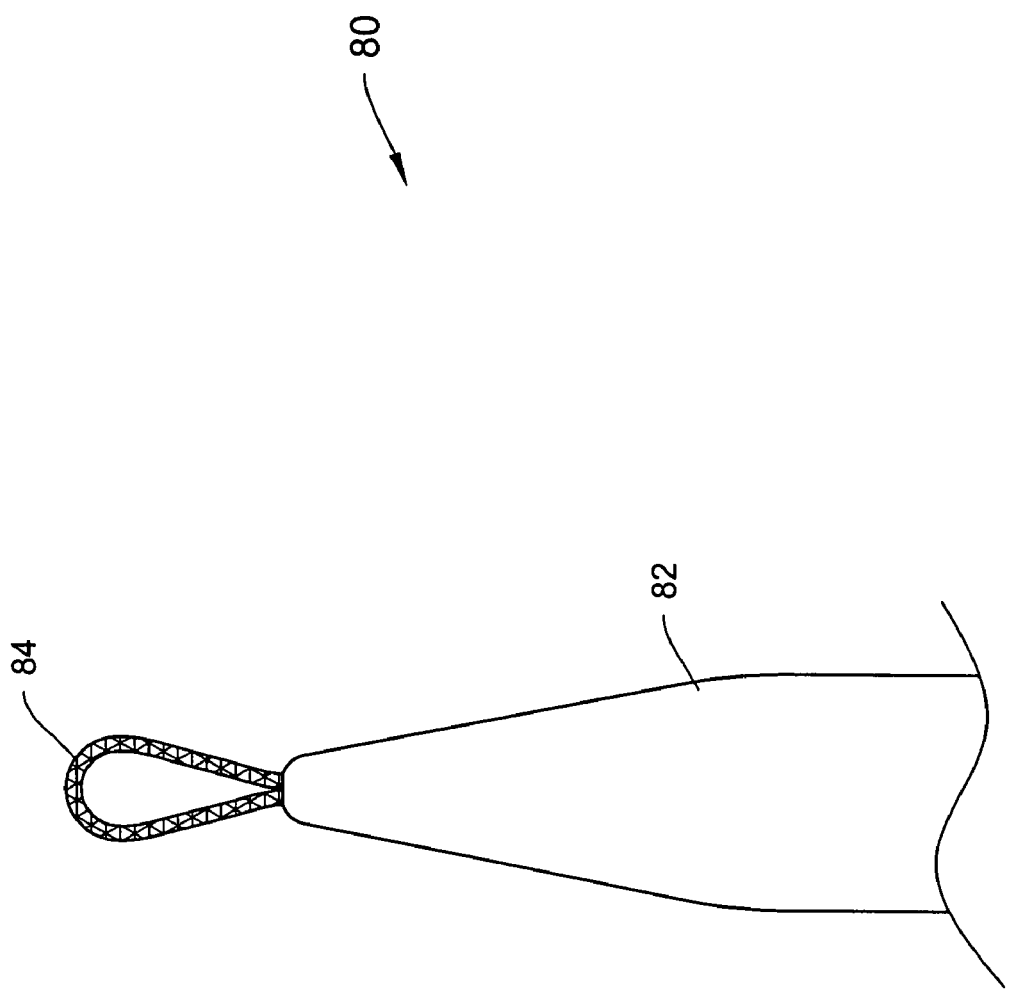
FIG. 8 depicts an association loop affixed into a dilator assembly and formed from a braided tubular filament according to another illustrative embodiment of the invention.

FIG. 8 depicts another dilator assembly 80 having an association loop 84 affixed at a leading end of a dilator 82. A unique aspect of this embodiment is that the association loop 84 is formed from a multi-stranded filament. In the depicted embodiment, the multiple strands are braided to form a hollow tube. When the braided association loop 84 is tensioned, the inner and outer cross-sectional diameters of the loop filament become smaller, while the length of the loop 84 increases. The association loop 84 and dilator 82 may be associated with any complementary structure on a delivery device, such as any of those described herein. One advantage of this configuration, referring also to FIGS. 13-23B, is that the association loop 84 may be tensioned during insertion into a suitable slot or notch. Such tensioning causes the diameter of the loop filament to decrease and more easily fit into the notch or slot. Another advantage is that once tensioning is removed, the loop filament tends to expand back to its steady state diameter, thus impeding it from easily sliding out of a suitably sized notch or slot in a delivery device.

Figure 9:
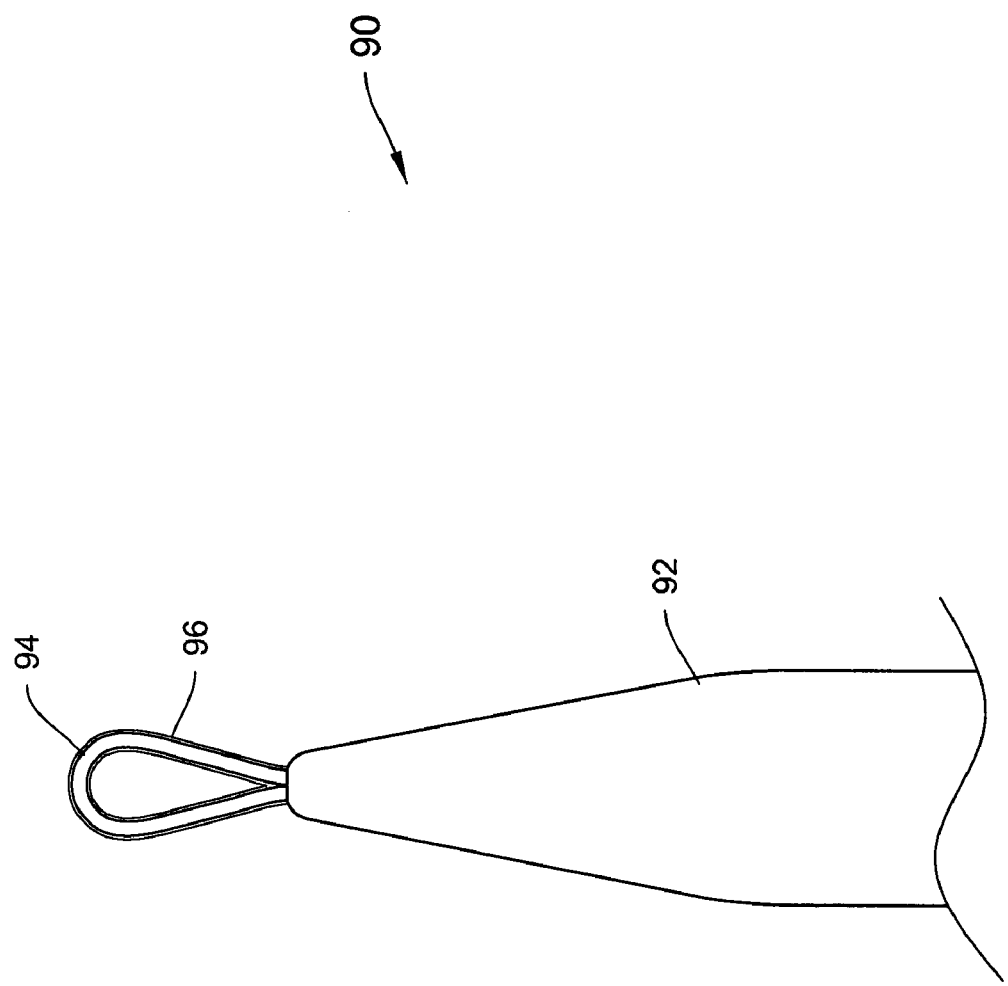
FIG. 9 depicts an association loop affixed into a dilator assembly and including a coating according to another illustrative embodiment of the invention.

FIG. 9 depicts another illustrative embodiment of dilator assembly 90 including an association loop 94 according to an illustrative embodiment of the invention. As in the previously discussed embodiments, the association loop 94 is affixed in some suitable fashion within the dilator 92. In the depicted example of FIG. 9, the association loop filament may be single or multi-stranded. If multi-stranded, it may be configured in any suitable manner, including the above described twisted, braided, and/or hollow tubular manner. As an additional feature, the loop filament of FIG. 9 includes a coating 96. The coating 96 may be formed, for example, from a suitable elastic material, such as silicone.

According to one configuration, the diameter of the coated loop 94 is sized to be smaller than the outer diameter of a shaft of a delivery device. In operation, as the loop 94 is placed over a tapered distal tip, as shown in FIG. 13, the compressible coating 96 on the association loop 94 contracts to allow the association loop 94 to interfit over the distal end of a delivery device shaft.

According to another illustrative example, the coated association loop 94 has a cross-sectional diameter that is larger than the width of a slot on a delivery device shaft. In this example, and as in the case of the FIG. 8 braided embodiment, the association loop filament can compress to interfit into the slot. Then, the tendency for the compressed coating to return to its normal uncompressed state acts to impede, and in some configurations prohibit, the association loop 94 from falling out of the slot and becoming disassociated with the delivery device.

Figure 10:
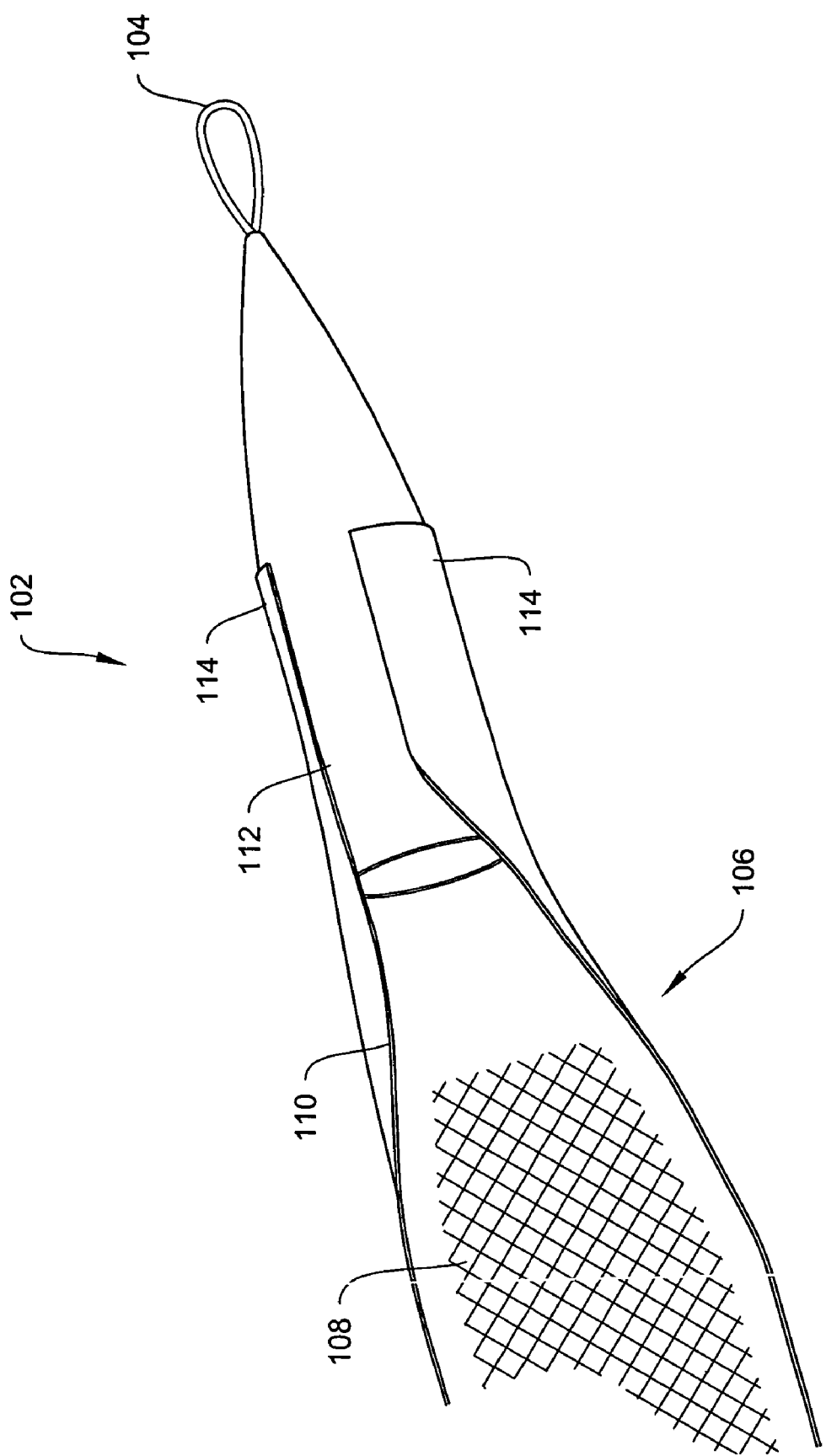
FIG. 10 shows a sling assembly end with a sleeve attached to an association loop via a dilator assembly according to an illustrative embodiment of the invention.

FIG. 10 shows a dilator assembly 102, including an association loop 104 of the type described above, affixed to an end of a sling assembly 106 according to an illustrative embodiment of the invention. As shown, the exemplary sling assembly 106 includes a mesh sling 108 and a protective sleeve 110. The mesh sling 108 is free floating in that it does not attach to anything, including the protective sleeve 110 or the dilator assembly 102. The end 114 of the sleeve 110 wraps around and is heat-bonded to a substantially cylindrical trailing portion 112 of the dilator assembly 102. To heat bond the sleeve end 114 to the dilator portion 112, the plane of the association loop 104 is first oriented to the plane of the sleeve 110, for example, either substantially parallel, perpendicular, or any other any angle, to the sleeve 110. The sleeve end 114 is flattened and the dilator portion 112 is placed on top of the sleeve end 114. The sleeve end 110 is then wrapped around the dilator portion 112 to form a "U" or "C" shape, and heat is applied to bond the sleeve end 114 onto the surface of the dilator portion 112. In an alternative embodiment, a piece of heat shrink tubing can be placed over the sleeve end 114 and the dilator portion 112 prior to the application of heat to bond the sleeve 110 to the dilator assembly 102. It should be noted that any suitable method may be used to attach the sleeve to the dilator assembly, for example, heat bonding, gluing, stapling, stitching, etc.

In other embodiments, the sleeve end may have a width larger than the circumference of the dilator. The sleeve end may be wrapped around the dilator and the sides of the sleeve end may overlap each other. The width of the sleeve end may also be reduced, for example, by folding or trimming, such that the sleeve end encircles the dilator fully at most once, and without overlap. It is preferred that the attachment of the sleeve end to the dilator not substantially add to the size or profile of the dilator as a smaller profile is perceived to be safer during delivery of an implantable sling assembly.

Figure 11:
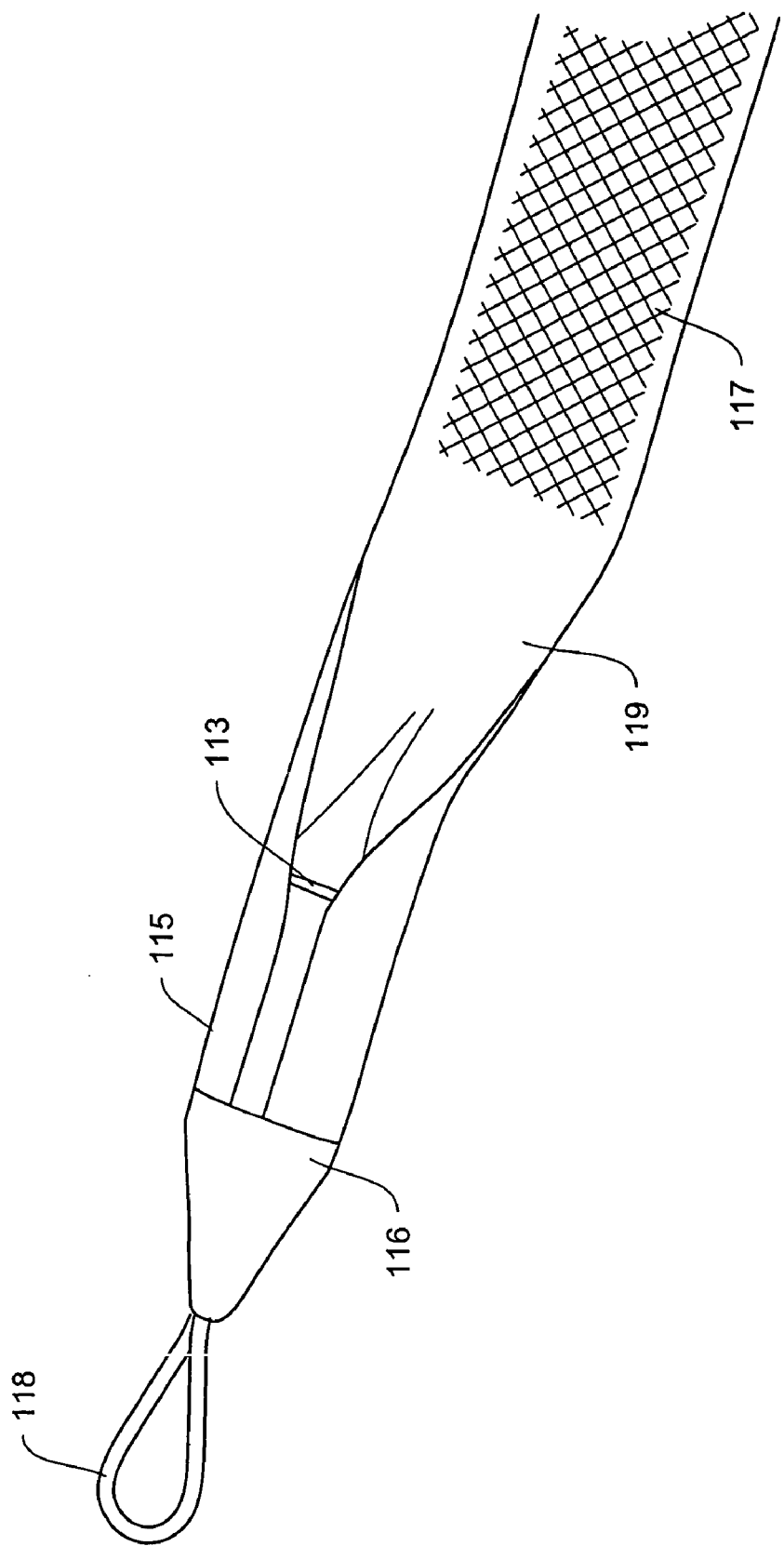
FIG. 11 shows a sling assembly end with a sleeve attached to an association loop via a dilator assembly according to another illustrative embodiment of the invention.

FIG. 11 depicts another method of bonding a sleeve end 115 to a dilator assembly 116. Instead of just wrapping the sleeve end 115 around the dilator trailing portion 113, the dilator trailing portion 113 is first inserted into the sleeve end 115. More specifically, the plane of the association loop 118 is first oriented to the plane of the sleeve 119, for example, either substantially parallel, perpendicular, or any other any angle, to the sleeve 119. The trailing portion 113 of the dilator assembly 116 is then inserted into the sleeve end 115. The sleeve end 115 is then pulled tightly around the dilator trailing portion 113, and heat is applied to bond the sleeve end 115 to the surface of the dilator trailing portion 113. In an alternative embodiment, a piece of heat shrink tubing is then inserted over the sleeve end 115 and heated to bond the sleeve end 115 to the surface of the dilator trailing portion 113.

Although the preferred illustrative embodiments of FIGS. 10 and 11 depict the sling assembly including a protective sleeve and the sling as being free floating, this need not be the case. In other illustrative embodiments, the protective sheath may be eliminated and the sling ends be bonded directly to the dilator assemblies. In other illustrative embodiments, the sling may be attached to the protective sleeve in any suitable fashion.

Additionally, any suitable sleeve and sling assemblies or slings known in the art can be used with the invention. For example, a sling mesh having tangs or projections that extend laterally from the edges of the sling along at least a portion of the length of the sling can be used. It is preferred that when the sling is placed in the body, the sling can lie somewhat flat to allow tissue ingrowth and the tanged portion of the sling to grip the tissue. In the embodiment where the sleeve or sling is thermobonded to the dilator, the dilator and the sling or sleeve are preferably made of a material which is compatible for thermobonding to achieve the maximum bond strength. An example of such a compatible thermobonding material is polyethylene. In an alternative embodiment, the sling or sleeve is glued to the dilator, for example, using cyanoacrylate. When gluing with cyanacrylate, the dilator and the sleeve are preferably made of a plastic material such as nylon. Suitable sleeves and slings are disclosed in the documents listed herein above and incorporated by reference in their entirety.

Figure 12:
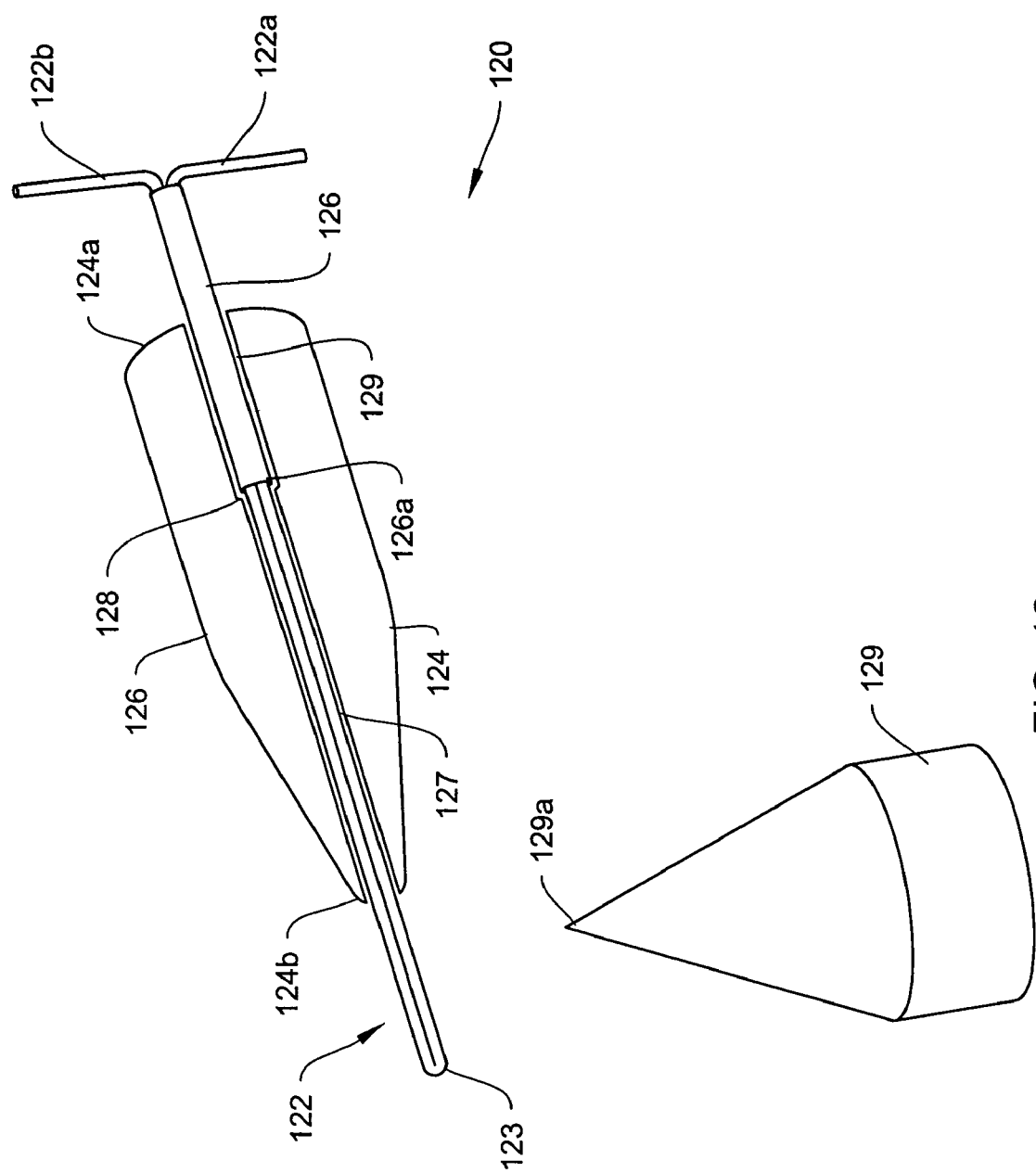
FIG. 12 shows a side view of an association loop affixed into a dilator assembly according to another illustrative embodiment of the invention.

The invention further includes methods of producing a mating structure, such as an association loop, on an implant assembly. FIG. 12 depicts another illustrative dilator assembly 120 including an association loop 122 formed into a tissue dilating structure 124. In addition to employing a crimp tube 126, such as the metal crimp tubes previously discussed, this illustrative configuration also bends the terminal ends 122a and 122b of the association loop filament at an angle to a longitudinal axis of the crimp tube 126. In a similar fashion to the embodiments of FIGS. 4 and 5, the dilator 124 includes two axially extending channels 127 and 129 in fluid communication with each other and interfacing at an intermediate shoulder 128.

According to one illustrative process, the association loop is flatted and interfitted through the crimp tube 126 as shown in FIG. 12. The leading end 123 of the flatted association loop 122 is then inserted into the channel 127 via the channel 129 at the trailing end 124a of the dilator 124. As the leading end 123 of the association loop 122 extends through an opening at the leading end 124b of the dilator 124, the leading end 126a of the crimp tube 126 abuts the shoulder 128, which stops the crimp tube 126 from passing into the channel 127. At this point, the excess ends 122a and 122b may be trimmed or cut off all together. Leaving some remnant of the ends 122a and 122b may be desirable to provide additional protection against the association loop 122 pulling out of the dilator 124.

Subsequent to the above described assembly, the association loop 122 can be expanded and shaped as desired. Preferably, the loop is shaped such that it cannot slip back into the dilator 124. In some configurations, neither the crimp tube 126 nor the association loop filament is affixed rotationally in the dilator 124. This feature enables the association loop 122 to rotate relative to the dilator 124, allowing the medical operator to twist and untwist a sling assembly while the loop 122 is associated with a delivery device.

According to another feature, the invention provides an association loop expansion tool of the type depicted at 129. To expand the association loop 122, the tip 129a of the loop expansion tool 129 is passed through the flatted association loop 122 to open it to a desired degree. In this embodiment, where the expansion tool 129 is conical in shape, an oval like association loop 122 is produced. However, the tool 129 can have any preferred profile or cross-section of choice, for example, triangular or rectangular to provided association loops of various shapes. One advantage of the conical design of the tool 129 is that it enables the association loop 122 to be opened to whatever degree is desired by the medical operator.

In an alternative embodiment, an association loop 122 and dilator assembly 120 can also be produced by inserting the two ends 122a and 122b of a flatted loop filament into the leading end 124b of the dilator 124. A crimp tube 126 can then be inserted onto the filament ends 122a and 122b and crimped at a given length. In this example, the filament ends 124a and 124b extend in a trailing direction and are not bend to form a T. The flatted association loop 122 and the dilator tube 126 are then pulled back towards the leading end 124b of the dilator 124 where the loop is formed to a preferred shape.

In another illustrative embodiment, a cavity of a dilator can be shaped to a desired configuration such as an oval cross-sectional configuration to prevent the crimped filament from rotating within the dilator and, thus, preventing the association loop from rotating outside the dilator. In another alternative embodiment, a cavity can be tapered such that when the crimp tube is pulled into the cavity, the cavity interferes with the crimp tube to prevent rotation of the association loop relative to the dilator.

The association loops and dilator assemblies depicted in FIGS. 1-12 have been described as having a generally oval shape. However, this need not be the case and the association loops of the invention may have any suitable shape, including without limitation, circular, rectangular, triangular, or any other suitable polygonal or curved shape. Additionally, the association loops described herein may be used in combination with any suitable complimentary mating structure located on a delivery device, for example, such as an appropriately sized and shaped slot in a distal end of a shaft of a delivery device. In the following illustrative description and accompanying drawings, the association loop 1 is used to illustrate the interaction of an association loop with a suitable mating structure located on a delivery device. Only the portion of the association loop 1 within the mating structure is depicted, e.g., a cross-sectional view of the association loop 1. Although the association loop 1 may be shown contacting the walls of the channels of the delivery devices, it is understood that the association loop may be sized smaller or larger than the width of the channels of the delivery devices, and that any suitable association loop may be employed, including without limitation, any of the illustrative association loops described herein.

A delivery device may be configured with a mating structure, such as a slot, which can cooperate with an association loop as described above. The slot can be positioned at any location along the delivery device, but is preferably located close to the distal tip of the delivery device. Some illustrative suitable delivery devices are disclosed in the documents listed herein above and incorporated by reference in their entirety. In one embodiment, the delivery device includes a shaft that can be used to penetrate tissue or fascia. The shaft can be made of rigid material or malleable material. The shaft can be pre-bent such that it defines a configuration that has one or more curves in a plane or the shaft can have one or more curves on multiple planes. Preferably, the delivery device has an opening into which the association loop can be inserted. In one illustrative embodiment, the opening is a slot defined by a channel having radially disposed and longitudinally disposed sections/legs. The slot can have any shape and can be substantially smooth or can include one or more dimples, grooves, protuberances and/or indentations or other irregularities, formed either during the manufacture of the slot or by attaching an implant to the slot wall. Preferably, the slot is shaped such that it impedes, and in some cases prohibits, the loop from easily unhooking and disassociating from the slot.

FIG. 13, for example, depicts an L-shaped slot 132 positioned near a distal end 130 of a delivery device shaft 134. The L-shaped slot 132 is formed from a first channel 133 extending radially into the shaft 134, and a second channel 135 extending distally along the axis 136 of the shaft 134 from an inner terminal end 133*a* of the first channel 133. An association loop, such as the associate loop 1 of FIG. 1, can slide radially into the opening 133*b* of the first channel 133 and along the first channel 133 to the inner terminal end 133*a*. The association loop 1 can then slide distally along the second channel 135 to the most distal end 135*a* of the second channel 135 to hook one end of the implant assembly 10 of FIG. 1 onto the distal end 130 of the shaft 134. During a sling placement procedure, this process may be repeated with the second association loop 3 and the same or a second similar delivery device.

According to the illustrative embodiment of FIG. 13, the first radially extending channel 133 may be about 1 mm, 1.5 mm, 2 mm, or about 2.5 mm in length and about 0.5 mm, 0.75 mm, 1 mm, or about 1.5 mm in width, and the second axially extending channel 135 may be about 3 mm, 4 mm, 5 mm or about 6 mm in length and about 0.5 mm, 0.75 mm, 1 mm, or about 1.5 mm in width. The shape and/or dimensions (e.g., width, length or diameter) of the slot 132 may be varied to suit the dimensions or intended orientation of the association loop on the implant assembly.

An advantageous feature of the L-shaped slot 132 is that the association loop 1 slides easily into the first channel 133 and remains free to slide along the second channel 135. When slid to a proximal most position 133*a* in the second channel 135, the association loop 1 may be slid radially out of the first channel 133 to unhook the association loop 1 and thus, the implant assembly 10, from the shaft 134 with a minimum of effort. Alternatively, in response to pulling the shaft in a proximal direction (a motion typically employed in a abdominally initiated sling implantation procedure when withdrawing a delivery device to pull an end of a sling assembly up through the abdomen via an incision in the vaginal wall of a patient), the distally extending orientation of the second channel 135 causes the association loop 1 to slide to the distal most position 135*a* in the L-shaped slot 132. This tends to maintain the association loop 1, and thus the implant assembly 10, hooked onto the L-shaped slot 132 during withdrawal of the shaft 134 in a proximal direction.

FIG. 14 depicts an alternate embodiment of an L-shaped slot 142 formed in a distal end 144 of a shaft 146 of a delivery device. The L-shaped slot 142 is similar to the L-shaped slot 132 in that it includes a first radially extending channel 143 and a second axially extending channel 145. As an additional feature, the radially extending channel 143 includes an indentation 147 extending axially in a proximal direction. The indentation is sized and shaped to seat the association loop 1 to impede, and in some cases prohibit, it from sliding radially out of the channel 143. As a further feature, the axially extending channel 145 includes a width narrowing protuberance 149 located at its proximal most end. The protuberance 149 is sized to impede, and in some configurations to prohibit, the association loop 1, subsequent to insertion into the channel 145, from sliding in a proximal direction along the channel 145 sufficiently far to enable it to enter the radially extending channel 143. In this way, the protuberance 149 also impedes, and in some configurations prohibits, the association loop 1 from becoming unhooked from the shaft 146.

FIG. 15 depicts another illustrative embodiment of an L-shaped slot 150 in a distal end 154 of a shaft 156. As in the previously discussed embodiments, the slot 150 includes a radially extending channel 151 and an axially extending channel 152. A feature of the illustrative embodiment of FIG. 15 is that the axially extending channel 152 has a width that is both smaller than the width of the radially extending channel 151 and less than a normal uncompressed diameter of the filament forming the association loop 1. In operation, the association loop 1 slides freely into the radially extending channel 151, but is compressed when slid into the axially extending channel 152. This compression causes an increased friction between the association loop 1 and the axially extending channel 152, which tends to maintain the association loop 1 within the axially extending channel 152.

FIG. 16 depicts a further alternative embodiment of an L-shaped slot 160 located at the distal end 162 of a delivery device shaft 164. A feature of this embodiment is that the axially extending channel 168 tapers inward as it extends distally. The taper reduces the width of the channel 168 sufficiently near its distal end 168*a* to compress the filament of the association loop 1 when the association loop 1 is pulled distally toward the tapered distal end 168a of the second channel 168. This tends to inhibit the association loop 1 from sliding proximally along the channel 168 and becoming unhooked from the shaft 164.

The resiliency and flexibility of the material forming and/or coating the association loop 1 contribute to the force holding the association loop 1 in place near the distal end 168a of the tapered second channel 168. For example, an association loop 1 formed from a strand of metal wire may not easily compress and become lodged in the tapered second channel 168. However, an association loop 1 formed from multiple strands of wire and/or coated with a flexible or resilient material, such as a polymer, may compress and lodge more securely in the tapered second channel 168. This type of association loop may require more force to pull the association loop out of the channel 168.

FIG. 17 depicts another alternative embodiment of an L-shaped slot 170 formed in a distal end 176 of a delivery device shaft 178. As in the previously discussed embodiments, the slot 170 includes a radially extending channel 172 and an axially extending channel 174. One feature of this illustrative embodiment is that the opening 173 to the radially extending channel 172 is enlarged for easy insertion of the association loop 1. More specifically, the wall 172a of the radially extending channel 172 tapers outward to create to the enlarged opening 173. According to the illustrative embodiment, the width of the radially extending channel 172 at all locations is larger than the outside diameter of the association loop filament. According to another feature of this embodiment, in a similar fashion to the axially extending channel 152 of FIG. 15, the axially extending channel 174 has a width less than the outside diameter of the association loop filament. The combination of the enlarged opening 173 of the channel 172 and the reduced width of the channel 174 facilitates hooking the association loop 1 into the L-slot 170 and, at the same time, impedes, and in some configuration prohibits, the association loop 1 from becoming unhooked.

FIG. 18 depicts another alternative embodiment slot structure 180 in a distal end 186 of a delivery device shaft 188. In contrast to previous L-shaped slots, the slot structure 180 of FIG. 18 is T-shaped, including a radially extending channel 182 and an axially extending channel 184. As in the case of the previously discussed L-shaped slots, the axially extending channel 184 includes a distally extending channel portion 184a. However, in addition, in the slot structure 180, the axially extending channel 184 also includes a proximally extending channel portion 184b. One advantage of the T-shaped structure 180 is that it tends to cause the association loop 1 to remain within channel 184 regardless of whether the shaft 188 is moved in the proximal direction or the distal direction. More specifically, in response to the delivery device shaft 188 being inserted into a patient's body and moved in a distal direction, the association loop 1 tends to slide into the channel portion 184b. Alternatively, in response to moving the shaft in the proximal direction, the association loop tends to slide into the channel portion 184a. In either case, the association loop 1 tends to stay hooked within the structure 180. It should be noted that any of the previously described modifications to the dimensions of the L-shaped slot may also be applied to the T-shaped slot of FIG. 18.

The association loop 1 is may be unhooked from the T-shaped slot 180 by positioning the association loop 1 at the inner terminal end of the radially extending channel 182 and sliding the association loop 1 radially out of the slot 180.

As now described, the invention also may include a structure that overhangs the entrance to the L- or T-shaped slot to further reduce the likelihood of the association loop inadvertently coming unhooked from the delivery device shaft. Preferably, such structures are deformable to the degree that they do not prohibit the association loop from coming unhooked, but instead impedes its exit from the L- or T-shaped slot. However, in alternative configurations, such structures may be sufficiently rigid to prohibit the association loop from coming unhooked. In various illustrative embodiments, the overhanging structure takes the form of a sheath or tube having a portion placed over a portion of the radially extending channel opening. The structures discussed below can be employed, for example, with any of the slot structures discussed above. In one illustrative embodiment, the below discussed structures are formed as a coating on the delivery device shaft. In other illustrative embodiments, they may be formed from a heat-shrink tubing cut to a suitable shape and interfitted over the delivery device shaft. The overhanging structures may be formed from a variety of flexible and/or resilient materials, such as a polymer plastic. Preferably, they are fixedly attached to the delivery device shaft, and may in some embodiments, be colored to increase visibility and/or can be made lubricious to aid the delivery device shaft in traversing tissue in the body.

Figure 19:
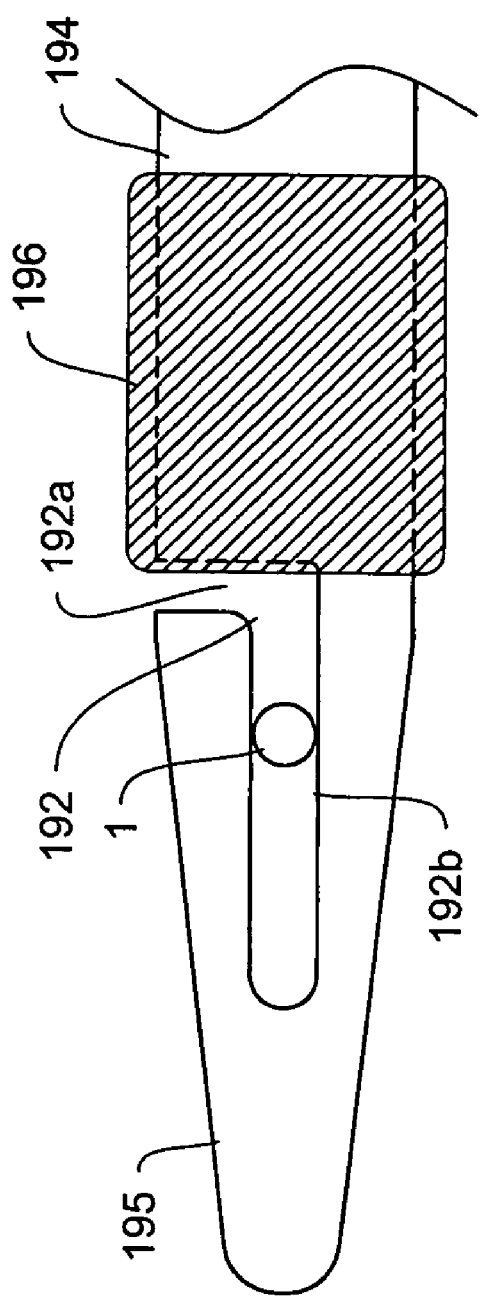
FIG. 19 shows the L-slot structure of FIG. 13 including a sheath partially extending over the opening to the radially extending leg according to an illustrative embodiment of the invention.

FIG. 19 is a longitudinal cross-sectional view of a delivery device shaft 194 having an L-shaped slot 192 of the type described above formed in a distal portion 195. A sheath 196 interfits over a portion of the delivery device shaft 194 and extends partially over the opening to the radially extending channel 192a. In this illustrative embodiment, the sheath is flexible enough to deflect sufficiently to allow the association loop 1 to enter the channel 192a, but rigid enough to impede, and in some configurations prohibit, the association loop 1 from sliding out of the channel 192a once inserted. The sheath structure of FIG. 19 may be employed with any of the above described slot structures.

Figure 20:
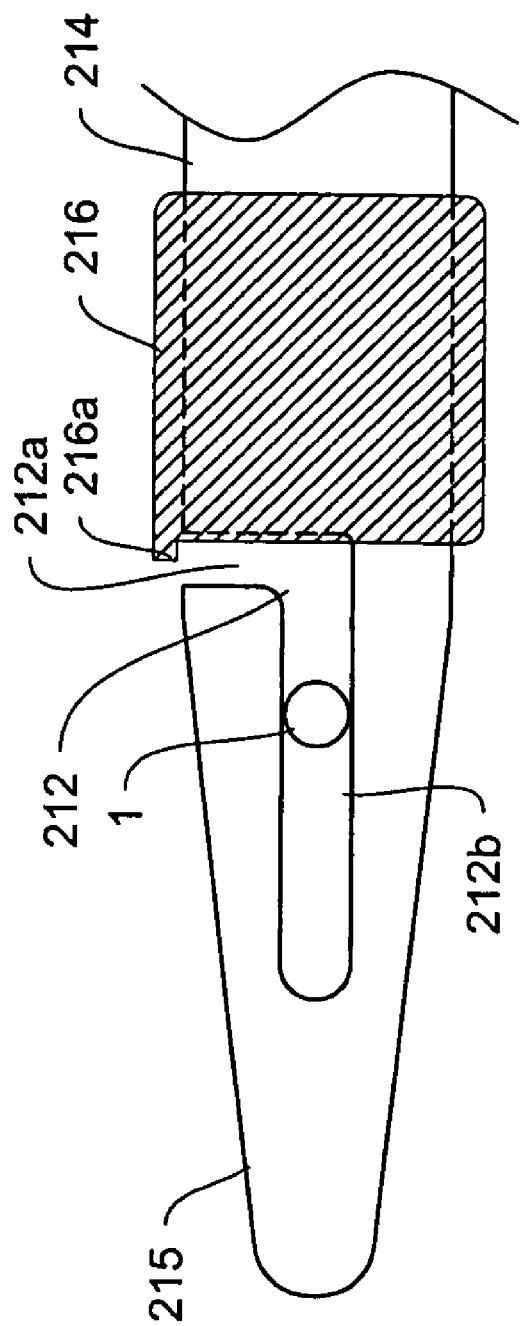
FIG. 20 shows the L-slot structure of FIG. 13 including another illustrative embodiment of a sheath that partially extends over the opening to the radially extending leg.

FIG. 20 depicts a cross-sectional view of another L-shaped slot structure 212 formed in a distal end 215 of a delivery device shaft 214. As depicted, the L-shaped slot 212 includes both a radially extending channel 212a and an axially extending channel 212b. The illustrative embodiment of FIG. 20 also includes a sheath 216 interfitted over the shaft 214 and located on the proximal side of the channel 212a. The illustrative sheath 216 includes a flap 216a, which extends axially in a distal direction to at least partially overlap with the opening to the radially extending channel 212a. The extension flap 216a is flexible enough to deflect inward toward the axially extending channel 212b to enable a medical operator to insert the association loop 1 into the radially extending channel 212a. However, the extension flap 216a is also rigid enough to impede, and in some configurations prohibit, the association loop 1 from sliding out of the first channel 212a subsequent to insertion. As in the case of the structure 196 of FIG. 19, the structure 216a may be sized and shaped to be employed with any suitable slot structure, including any of those described herein. Additionally, the extension flap 216a need not be supported with the sleeve 216, but instead may be supported in place with any suitable structure.

FIG. 21 depicts another illustrative L-shaped slot structure 232 formed in a distal end 234 of a delivery device shaft 236. The illustrative embodiment of FIG. 21 also includes a sheath 238 interfitted over the delivery device shaft 236. The sheath 238 includes a slotted portion 240 that aligns with the radially extending channel 232a. As shown, the slotted portion 240 is defined by the sheath walls 240a and 240b, and is narrower than the radially extending channel 232a, and preferably narrower than the diameter of the filament forming the association loop 1. According to the illustrative embodiment, the sheath walls 240a and 240b are sufficiently resilient to deflect outward to enable expansion of the slot 240 and insertion of the association loop 1. Subsequent to association loop 1 insertion, the sheath walls 240a and 240b expand back to a normal position to impede, and in some configurations prohibit, the association loop 1 from sliding back out the radially extending channel 232a. As depicted, the sheath 238 also includes an axially extending slotted portion 239 for enabling the association loop 1 to slide distally into the axially extending channel 232b. Although the axially extending slotted portion 239 is depicted as having the same width as the channel 232b, this need not be the case. The axially extending slotted portion 239 of the sheath 238 may have a larger width or, in some configurations, a smaller width to further impede the association loop 1 from unhooking from the slot 232.

It is to be understood that a sheath interfitted over a delivery device shaft as described above may have other configurations. For example, a hood portion 240c of the sheath 238, including sheath wall 240a, need not be present. Instead, the sheath wall 240b may act alone to impede, and in some configurations prohibit, the association loop 1 from sliding back out the radially extending channel 232a.

FIG. 22 depicts another illustrative slot and sheath combination 242. The illustrative embodiment 242 is substantially the same as the illustrative embodiment of FIG. 21, except that the sheath 246 includes a curved slotted section 248. The curved slotted section 248 preferably aligns with the radially extending channel 244a. The curved nature of the slotted section 248 acts both to ease the insertion of the association loop 1 into the L-shaped slot 244 and to reduce the likelihood of the association loop 1 sliding back out of the radially extending channel 244a.

The sheath portions 248a and 248b that form the curved slotted section 248 accomplish this by cooperating to constrain the association loop 1, when inserted into the slot 244, from re-entering the radially extending channel 244a. More specifically, in this embodiment, the sheath portion 248b extends across the inner terminal end of the channel 244a into the channel 244b. The sheath portion 248b thus acts as a flap. For example, when the association loop 1 is slid into the channel 244a, the sheath portion 248b deflects downward to allow the association loop 1 to slide into the channel 244b. The sheath portion 248b then prevents the association loop 1 from exiting the channel 244b because, as the association loop 1 is pulled into the channel 244a, the sheath portion 248b deflects against the wall of the channel 244b to block the entrance to the channel 244a.

Figure 23A:
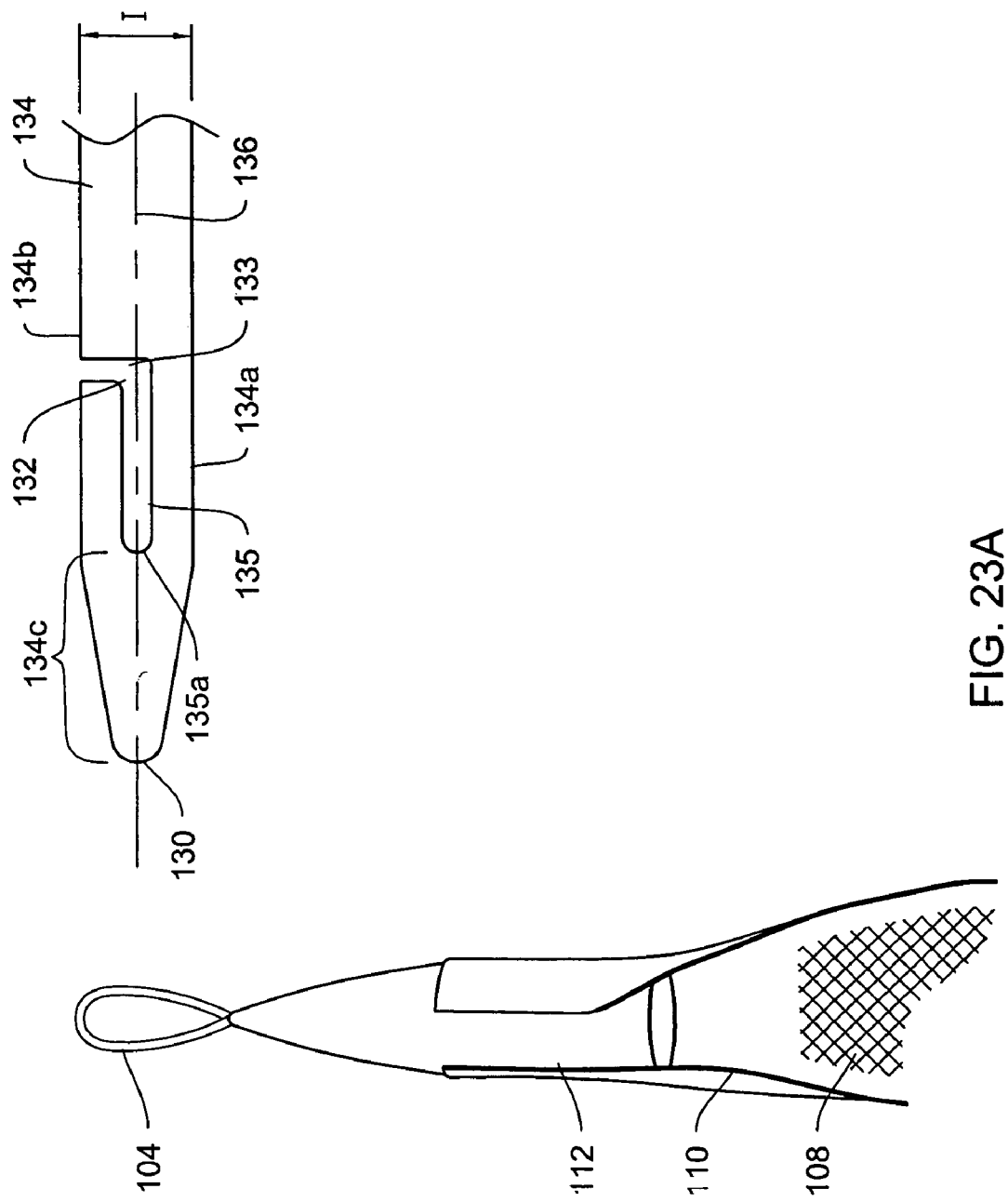
FIG. 23A shows an association loop at the end of a sling assembly prior to association with an L-slot on the end of a delivery device according to an illustrative embodiment of the invention.
Figure 23B:
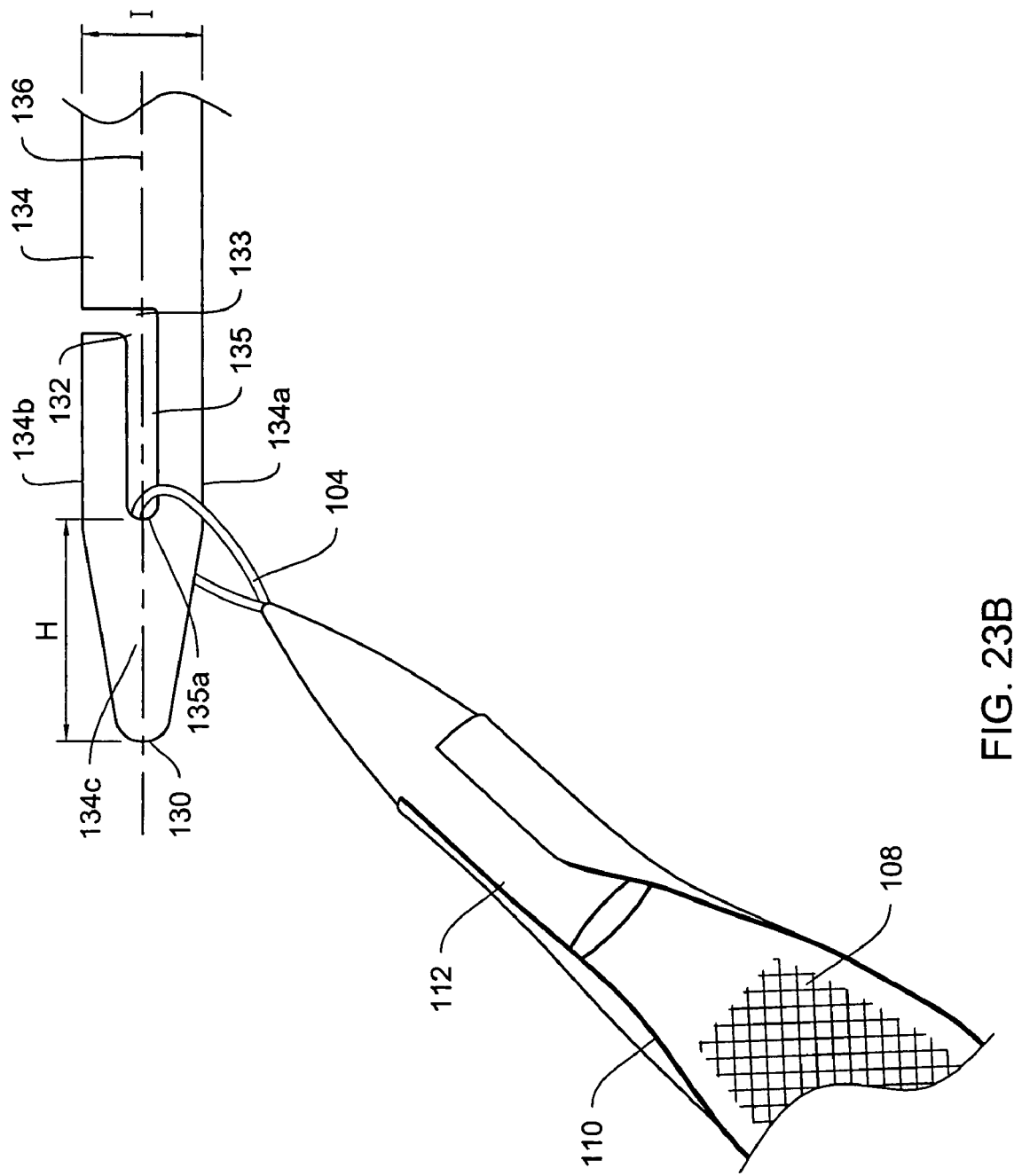
FIG. 23B shows an association loop of a sling assembly hooked into the axially extending leg of the L-slot on the end of a delivery device according to an illustrative embodiment of the invention.

Any of the above described association loop and dilator assemblies of FIGS. 1-9 and L- or T-shaped slots of FIGS. 13-22 may be used in combination and coordinated to ease insertion of an association loop into a slot, restrict or allow freedom of movement of the association loop within the slot, and impede the association loop from becoming unhooked from the slot. The dimensions of an association loop and a slot may be coordinated to facilitate the above. FIGS. 23A and 23B illustrate the interaction between an association loop on an end of a sling assembly and a slot near a distal end of a delivery device. Specifically, FIGS. 23A and 23B use the loop and dilator structure of FIG. 10 and a shaft 134 of the delivery device of FIG. 13 for demonstrating the coordination of the dimensions of an association loop and a slot on a delivery device.

FIG. 23A depicts the loop and dilator structure of the implant assembly of FIG. 10 and a slot 132 near the distal end 130 of the shaft 134 of FIG. 13 before the mating structures, e.g., the association loop 104 and the slot 132, are associated. The association loop 104 may be sized such that it has a diameter larger than or equal to the diameter I of the shaft 134 such that the association loop 104 may be slid over the distal end 130 of the delivery device shaft 134. The association loop 104, and thus, one end of a sling assembly, is hooked onto the shaft 134 by radially sliding the association loop 104 into channel 133 and axially sliding the association loop 104 to a distal end 135a of the channel 135.

FIG. 23B depicts the association loop 104 hooked onto the second channel 135 of the L-shaped slot 132. The loop 104, when positioned at the distal end 135a of the second channel 135, is constrained in the slot 132. As depicted, the loop 104 has a length sufficiently large to slide over the delivery device 134 and sufficiently short that a portion 134c of the delivery device 134 (from the distal end 135a of the axial channel 135 to the distal tip 130 of the shaft 134) prevents the dilator 112 from crossing the axis 136 around the distal tip 130 of the shaft 134. Even when the dilator 112 is pulled to extend the association loop 104 as far as possible, the length H of the portion 134c of the shaft 134 is longer that the association loop 104 and keeps the dilator 112 on a side 134a of the shaft 134. The diameter I and the length H of the portion 134c of the shaft 134 and the length of the association loop 104 all may vary yet still be selected relative to each other to maintain the dilator 112 on one side, e.g., side 134a of the shaft 134. This feature allows the loop 104 to be removed in specific directions. For example, to remove the loop 104 from the shaft 134, the loop 104 is slid towards the proximal most position in the second channel 135, is rotated 180 degrees around the axis 136 of the shaft 134 to remove the association loop 104 from the L-shaped slot 132, and slid back off the distal tip 130 of the shaft 134. When the association loop 104 is rotated 180 degrees around the delivery device shaft 134, the association loop 104 encircles the shaft 134 and the distal tip of the dilator 112 points towards the opening of the L-shaped slot 132.

In an alternative embodiment, the diameter I and the length H of the portion 134c of the shaft 134 and the length of the association loop 104 may be varied so that the dilator 112 may crossing the axis 136 around the distal tip 130 of the delivery device shaft 134 to a side 134b. For example, the length of the association loop 104 may be selected to be long enough to that portion 134c does not prevent the dilator 112 from crossing the axis 136 around the distal tip 130. In another embodiment, the length of the association loop 104 may be selected to be long enough to that portion 134C prevents the dilator 112 from crossing the axis 136 around the distal tip 130 of the shaft 134 when the association loop 104 is not fully extended. However, when the dilator 112 is pulled to extend the association loop 104, the association loop 104 becomes longer than the length H of the portion 134c of the shaft 134 and allows the dilator 112 to cross the axis 136 around the distal tip 130 of the delivery device shaft 134 from side 134a to side 134b.

Figure 24:
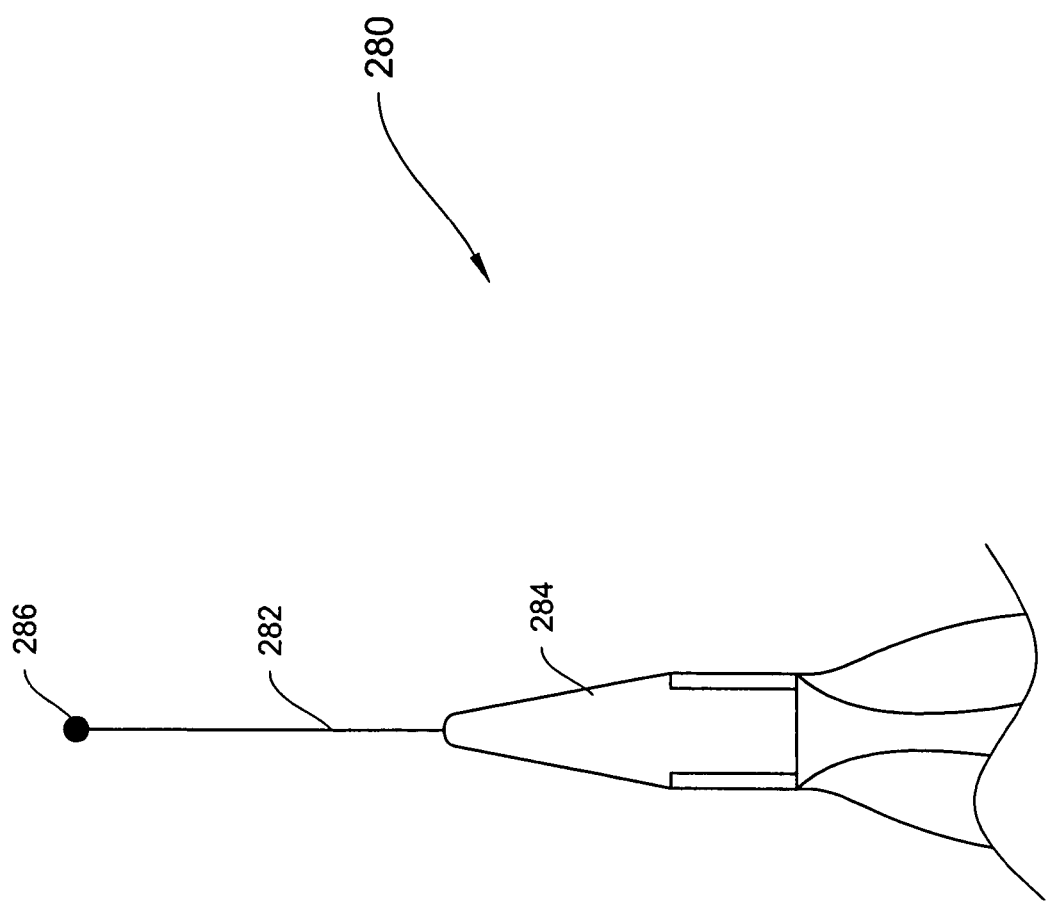
FIG. 24 depicts a ball-shaped association member extending from a dilator assembly according to another illustrative embodiment of the invention.

FIG. 24 shows another embodiment of a structure, a ball anchor-dilator assembly 280, that can be attached to an end of a sling assembly. In this embodiment, a wire 282 extends from a dilator 284 and terminates in a ball anchor 286. The ball anchor 286 can be attached to the end of the wire 282 or it can be molded to the end of a wire 282. The ball anchor 286 can be rigid or elastic. Although the anchor is depicted in the shape of a ball, it is understood that the anchor may be any regular or irregular shape, such as crescent, square, rectangular, bar, star, etc.

Figure 25:
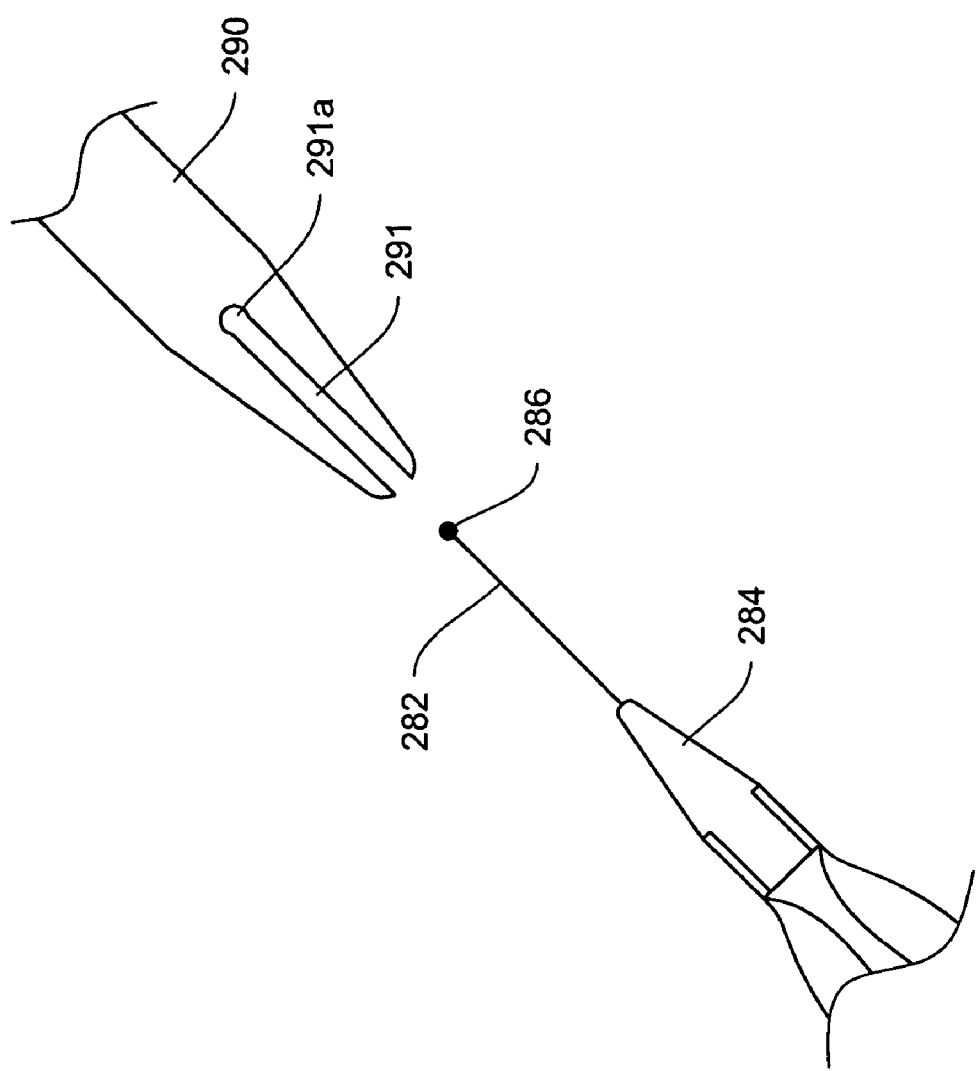
FIG. 25 shows the ball-shaped association member of FIG. 28 associating with a corresponding illustrative structure on a delivery device for placement of an implantable sling.

FIG. 25 depicts the ball-dilator assembly 280 and a complementary structure near the distal end of the shaft 290. As depicted, the shaft 290 can be constructed such that it has a ball receiving slot 291 located near the distal tip of the delivery device 290. The ball anchor may be snapped or otherwise inserted into the proximal end 291a of the slot 291.

In one embodiment, where an elastic ball is used as the ball anchor 286, the proximal end 291a of the slot 291 for receiving the ball anchor 286 has a size smaller than the size of the ball anchor 286. In this embodiment, the ball anchor 286 is compressed as it is inserted into the proximal end 291a of the slot 291 and expands in the ball-shaped proximal end 291a of the slot 291 when inserted to prevent the ball anchor 286 from inadvertently separating from the proximal end 291a of the slot 291.

In an alternative embodiment where the ball anchor 286 is rigid, the proximal end 291a of the slot 291 in the delivery device 290 may be made to the size of the ball anchor 286 and the ball anchor 286 is made to snap into the proximal end 291a of the slot 291 of the delivery device 290.

It is to be understood that any of the slots described herein, such as slot/sheath combinations, slots of varying dimensions, and slots including indentations and/or protuberances may be employed in combination with any of the associations loops described herein. Furthermore, the above described illustrative structures may be employed with any of the described delivery devices, or others known in the art, including the suprapubic, transobtural, and transvaginal delivery devices described below.

Figure 26:
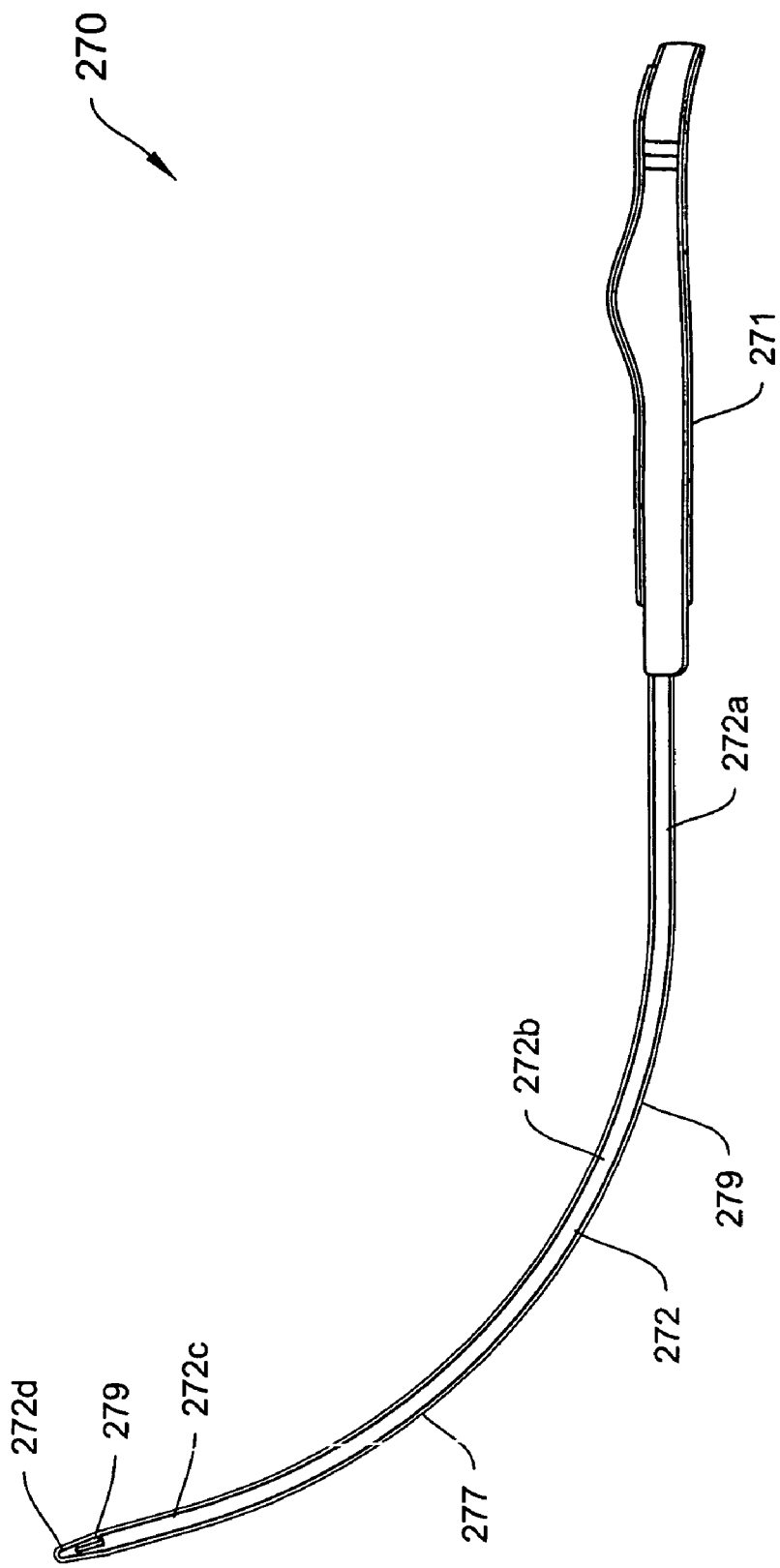
FIG. 26 depicts a sling delivery system including a delivery device particularly sized and shaped for suprapubic sling delivery and having any suitable slot at a distal end according to an illustrative embodiment of the invention, and employable with any of the illustrative embodiments of the association loops of FIGS. 1-11.

FIG. 26 depicts a delivery device 270 for delivering a sling assembly, such as the sling assembly 10 depicted in FIG. 1, to an anatomical location in the body of a patient. The delivery device 270 includes a handle 271 and, extending from the handle 271, a needle shaft 272 which is composed of a first straight section 272a, a curved section 272b, and a second straight section 272c. The first straight section 272a of the shaft 272 is permanently affixed to and extends distally from a distal end of the handle 271. The curved section 272b of the shaft 272 extends distally from the first straight section 272a. The second straight section 272c extends distally from the curved section 272b, and terminates at a distal end to form a conical tip 272d. The shaft 272 of the delivery device 270 is formed of surgical grade stainless steel and, excluding the conical tip 272d, has a constant diameter along its length. An L-shaped slot 279, which may be any of the slot structures described herein, is positioned on the second straight section 272c near the distal end of the delivery device 270.

In use, the shaft 272 is employed to create a passage through body tissue, namely, from the abdomen to the vagina. An incision is made on each side of the midline of the body in the lower abdomen and an incision is made in the vaginal wall. The shaft 272 of the delivery device 270 is inserted through one abdominal incision down along the posterior surface of the pubic bone through the vaginal incision. An association loop, which may be any of the association loops described herein, slides into the L-shaped slot 279 to hook one end of a sling assembly onto the distal end of the shaft 272. This process may be repeated with a second association loop and the delivery device 270 or a second delivery device similar to or the same as delivery device 270 on the contralateral side of the body. With both delivery devices placed, cystoscopy may be performed to ensure bladder integrity. The two delivery devices 270 may be withdrawn from the abdominal incisions, drawing each end of the sling assembly through the respective passages created by the shafts of the delivery devices. The association loops are then unhooked from the respective delivery devices. The dilators may be used as handles to adjust the position of the sling assembly to achieve desired placement. Once desired placement of the sling assembly is achieved, the tabbed spacer, and thus the looped portion of the bottom side of the plastic sleeve, is cut. Then, by pulling upward on the dilators, the medical operator slides the plastic sleeve off the knitted mesh and removes it from the body. The delivery devices and the plastic sleeve, including the dilators, are then discarded.

In another aspect, the invention includes coloring the shaft of the delivery device so that that the needle shaft of the delivery device is visible. The shaft can be colored by either attaching a colored tubing or sheath, or by chemically coloring the shaft of the delivery device. A heat-shrink tubing 277 may be thermobonded to the needle shaft 272. As depicted, the heat-shrink tubing 277 can extend the length of the needle shaft 272 to act as a visible coating to aid the physician during cystoscopy. The colored heat-shrink tubing 277 can be configured to terminate at a location on the needle shaft 272 of the delivery device 270 that corresponds to the opening of the slot 279 and can thus serve to prevent the association loop from disengaging freely from the needle shaft 272. Alternatively, the heat-shrink tubing 277 can extend just partially along the length of the needle shaft 272. The colored needle shaft aids the user during cystoscopy. In another embodiment, an electrochemical process can be used to provide a colored finish on the needle shaft 272 of the delivery device 270 to facilitate needle visibility during cystoscopy. Any color can be used such as green, blue, yellow or orange. In one example, the finish includes a blue chrome oxide finish.

In an alternative embodiment, although not shown, the delivery device 270 of FIG. 26 may be configured for a transvaginal or a prepubic procedure. For example, the slot 279 may be oriented such that the axially extending channel of the slot 279 extends proximally towards the handle 271, instead of distally toward the distal end of the shaft 272. When configured for a transvaginal or a prepubic procedure, the delivery device may be shaped and sized the same as or differently from the delivery device 270 of FIG. 26. For example, the shaft 272 may be configured shorter than for a suprapubic procedure or incorporate a different curve radius. A transvaginal or a prepubic procedure is similar to suprapubic procedure described above, however, a sling assembly is hooked onto a delivery device via an association loop and then is inserted from a vaginal incision to an abdominal incision over or under the pubic bone.

Figure 27:
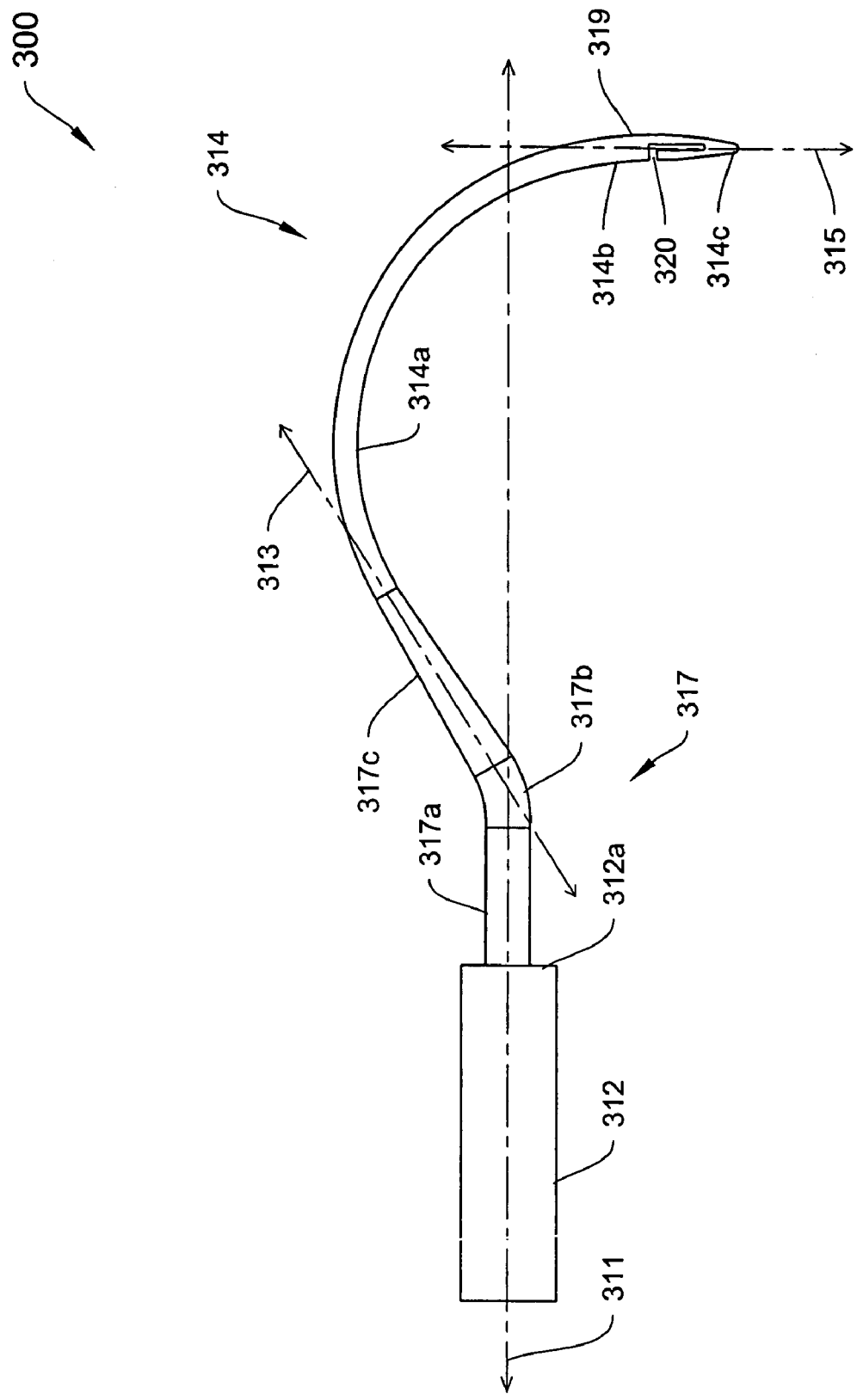
FIG. 27 shows another illustrative delivery device particularly sized and shaped for transobtural placement of an implantable sling and having any suitable slot at a distal end, and employable with any of the illustrative embodiments of the association loops of FIGS. 1-11.

FIG. 27 shows another illustrative delivery device 300 particularly sized and shaped for transobtural placement of an implantable sling, and employable with any of the illustrative embodiments of FIGS. 1-25. FIG. 30 depicts a side view of a delivery device 300 according an illustrative embodiment of the invention. The delivery device 300 includes a handle 312, a shaft 314, and a transitional portion 317 extending distally between a distal end 312a of the handle 312 and a proximal end of the shaft 314. The transitional portion 317 includes a first straight section 317a, a curved section 317b and a second straight section 317c, all lying substantially in a single plane, and may be formed as either part of the shaft 314 or as part of the handle 312. The shaft 314 includes a curved section 314a, a straight section 314b and a conical tip 314c, all lying substantially in the same plane as the transitional portion 317. In the illustrative embodiment, the first straight section 317a of the transitional portion 317 attaches to the distal end 312a of the handle 312, extends distally along a first axis 311, and preferably has a substantially constant diameter. The curved section 317b of the transitional portion 317 extends from a distal end of the first straight section 317a, curves away from the first axis 311, and also preferably has a substantially constant diameter. The second straight section 317c extends from a distal end of the curved section 317b along a second axis 313, and preferably has a diameter that decreases from its proximal end to its distal end to provide increased structural stability to the shaft 314. The curved section 314a, preferably, has a substantially constant diameter, smaller than the diameter of the curved section 317*b* of the transitional portion 317, and extends from the distal end of the second straight section 317*c* of the transitional portion 317, curves back toward the first axis 311, and terminates at a distal end approximately at an intersection with the first axis 311. The straight section 314*b*, preferably, has a substantially constant diameter and extends from the distal end of the curved section 314*a* along a third axis 315, which crosses the first axis 311. In one configuration, a conical tip 314*c* extends distally from the straight section 314*b*. In another configuration, the distal portion 319 of the delivery device 300 may include a structure or feature 320 for associating the delivery device 300 with a sling and/or sling assembly or an end of a sling and/or sling assembly, such as any of the slot structures described herein. The delivery device of FIG. 30 may be employed with any of the above described loop and dilator assemblies described herein.

In use, the shaft 314 is employed to create a passage through body tissue, namely, from just lateral to the inferior pubic ramus through the obturator foramen to the vagina. Three incisions are made to the body of the patient. A first incision is made just lateral to the inferior pubic ramus at the junction where the inferior pubic ramus and the adductor longus muscle meet. A second incision, corresponding to the first incision, is made on the contralateral side. A third incision is made in the anterior vaginal wall and dissected bilaterally to the interior portion of the inferior pubic ramus. The handle 312 is grasped in one hand, and the shaft 314 of the delivery device 300 is inserted through one ischiopubic incision in a downward motion, piercing the obturator muscle and obturator membrane. Then the handle 312 is turned to a position 45 degrees to the midline of the patient's body. A forefinger of the opposite hand is placed in the lateral dissection of the vaginal incision and on the distal end of the delivery device 300. The forefinger is used to guide the distal end of the shaft 314 around the inferior pubic ramus through the vaginal incision.

Next, a first association loop is slid over the distal end of the shaft 314 and into a slot 320 to hook one end of a sling assembly onto the delivery device 300. The delivery device 300 is then withdrawn from the ischiopubic incision, drawing one end of the sling assembly through the passage created by the shaft 314 of the delivery device 300. The association loop is then unhooked from the delivery device 300. This process is repeated with a second association loop and the delivery device 300, or a second delivery device the same as or similar to the delivery device 300, on the contralateral side of the body. A single cystoscopy may be performed at this time to ensure bladder integrity. Then the dilators may be used as handles to adjust the position of the sling assembly to achieve desired placement. Once desired placement of the sling assembly is achieved, the tabbed spacer, and thus the looped portion of the bottom side of the plastic sleeve, is cut. Then, by pulling upward on the dilators, the medical operator slides the plastic sleeve off the knitted mesh and removes it from the body. The delivery devices and the plastic sleeve, including the dilators, are then discarded.

Figures 28A, 28B, 28C:
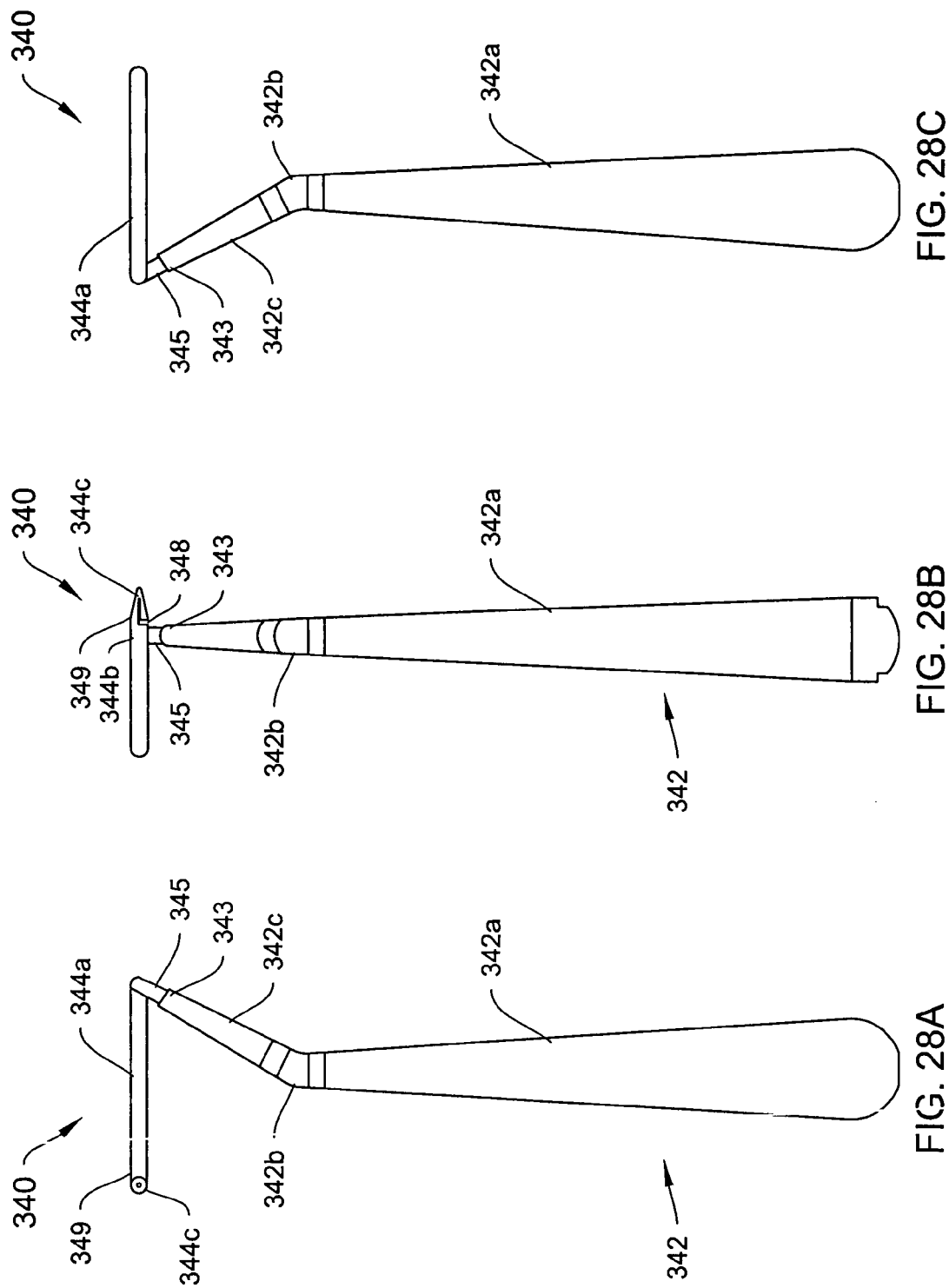
FIGS. 28A-28C show another illustrative delivery device also particularly sized and shaped for transobtural placement of an implantable sling and having any suitable slot at a distal end, and employable with any of the illustrative embodiments of the association loops of FIGS. 1-11.

FIGS. 28A, 28B and 28C show another illustrative delivery device 340 also particularly sized and shaped for transobtural placement of an implantable sling, and employable with any of the above described loop and dilator assemblies described herein, including those of FIGS. 2-9. The delivery device 340 includes a handle 342 with a first substantially straight section 342*a*, a curved section 342*b*, and a second substantially straight section 342*c* located substantially in a first plane, a transitional portion 345 extending out of a distal end 343 of the handle 342, and a shaft 344 extending from a distal end of the transitional portion 345. The shaft includes curved section 344*a*, a straight section 344*b*, and in one configuration, terminates in a conical tip 344*c*. The digital portion 349 of the delivery device 340 may include a structure or feature 348, for example, a slot structure as depicted in FIGS. 13-25, for associating the delivery device 340 with a sling and/or sling assembly or an end of a sling and/or sling assembly. The delivery device of FIGS. 28A, 28B and 28C may be employed with any of the above described loop and dilator assemblies described herein, including those of FIGS. 2-9.

The transitional portion 345 interfits and extends axially out of the distal end 343 of the second handle section 342*c* to affix the shaft 344 to the handle 342. As a result, the transitional portion 345 is substantially co-planar with the handle 342 in the first plane. The curved section 344*a* of the shaft 344 extends from a distal end of the transitional portion 345. The straight section 344*b* of the shaft 344 extends from a distal end of the curved section 344*a*. The curved section 344*a* and the straight section 344*b* are substantially coplanar in a second plane. According to the illustrative embodiment of FIGS. 28A, 28B and 28C, the first and second planes are substantially orthogonal to each other. However, the first and second planes may be at any suitable angle (e.g., about 10, 20, 30, 45, 60, 70 or 80 degrees) to each other.

To provide structural reinforcement, sections 342*b* and 342*c* have cross sectional diameters that taper to be smaller at the distal end 343 of the handle 342. Additionally, rather than having the tapered section 317*c* of the transitional portion 317 being formed as part of the shaft 314, as shown in FIG. 27, the tapered portions 342*b* and 342*c* of the embodiment of FIGS. 28A, 28B and 28C are formed as part of the handle 342. According to one feature, this configuration reduces the length of the transitional portion 345 and thus, provides improved structural support for the curved section 344*a*. Preferably, in operation, neither the handle 342 nor the intermediate/transitional portion 345 extends into the body of the patient, and provides a positive stop against this occurring.

In use, the shaft 344 is employed to create a passage through body tissue, namely, from just lateral to the inferior pubic ramus through the obturator foramen to the vagina. Three incisions are made to the body of the patient. A first incision is made just lateral to the inferior pubic ramus at the junction where the inferior pubic ramus and the adductor longus muscle meet. A second incision, corresponding to the first incision, is made on the contralateral side. A third incision is made and dissected bilaterally in the anterior vaginal wall. The handle 342 of the delivery device 340 is grasped in one hand, and the shaft 344 is inserted into the ischiopubic incision perpendicular to the skin with the first section 342*a* of the handle 342 at a 45-degree angle parallel with the thigh. A forefinger of the opposite hand is placed in the lateral dissection of the vaginal incision. The thumb of the opposite hand is placed on the outside of the curve of the shaft 344, and a downward force is applied, allowing the shaft 344 to pierce through the obturator foramen. The shaft 344 is then rotated medially around the inferior pubic ramus to meet the forefinger of the opposite hand, which guides the conical tip 349 of the shaft 344 through the vaginal incision. It is our understanding that during this procedure, the transition portion 345 does not extend into the ischiopubic incision.

Next, a first association loop is slid over the distal end of the shaft 344 and into a slot 348 to hook one end of a sling assembly onto the delivery device 340. The delivery device 340 is then withdrawn from the ischiopubic incision, drawing one end of the sling assembly through the passage created by the shaft 344 of the delivery device 340. The association loop is then unhooked from the delivery device 340. This process is repeated with a second association loop and the delivery device 340, or a second delivery device the same as or similar to the delivery device 340, on the contralateral side of the body. A single cystoscopy may be performed at this time to ensure bladder integrity. Then the dilators may be used as handles to adjust the position of the sling assembly to achieve desired placement. Once desired placement of the sling assembly is achieved, the tabbed spacer, and thus the looped portion of the bottom side of the plastic sleeve, is cut. Then, by pulling upward on the dilators, the medical operator slides the plastic sleeve off the knitted mesh and removes it from the body. The delivery devices and the plastic sleeve, including the dilators, are then discarded.

Preferably, the delivery devices and/or delivery assemblies of the invention are made of biocompatible materials, which can include, for example, polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. Preferably, a shaft of a delivery device of the invention is formed of surgical grade stainless steel.

The drawings are not necessarily to scale; emphasis instead is generally placed upon illustrating the principles of the invention.

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein above and incorporated by reference in their entirety. All operative combinations between the above described illustrative embodiments and those features described in U.S. patent application Ser. No. 10/642,365, entitled "Systems, methods and devices relating to delivery of medical implants," are considered to be potentially patentable embodiments of the invention.

What is claimed is:

1. A sling assembly comprising,
   a sleeve having a first end and a second end,
   a sling residing, at least partially, within the sleeve,
   a dilator having a first end and a second end and attached to the first end of the sleeve,
   an association loop extending into the second end of the dilator and located at a first end of the sling assembly and sized and shaped for associating the sling assembly with a shaft of a delivery device; and
   a spring loaded mounting arrangement to enable the association loop to extend and retract axially relative to the dilator.

2. The assembly of claim 1, wherein the association loop associates the sleeve with a delivery device.

3. The assembly of claim 1, wherein the loop is formed from a single strand of material.

4. The assembly of claim 3, wherein the strands of material is twisted.

5. The assembly of claim 1, wherein the loop is formed from multiple strands of material.

6. The assembly of claim 5, wherein the multiple strands are braided.

7. The assembly of claim 6, wherein the multiple strands form a hollow tube.

8. The assembly of claim 1, wherein the loop is coated with a shape retaining material.

9. The assembly of claim 1, wherein the loop is formed from metal.

10. The assembly of claim 1, wherein the loop is formed from polymer.

11. The assembly of claim 1, wherein the loop has two ends embedded along the length of the dilator.

12. The assembly of claim 1, comprising a fixed mounting arrangement between the dilator and the loop material within the dilator.

13. An implant delivery system comprising
    a sleeve having a first end and a second end and a sling residing at least partially within the sleeve, a dilator having a first end and a second end and attached to the first end of the sleeve, and an association loop extending into the second end of the dilator and located at a first end of the sling assembly,
    a spring loaded mounting arrangement to enable the loop to extend and retract axially relative to the dilator; and
    a delivery device onto which the association loop may be hooked.

14. The delivery system of claim 13, wherein the delivery device comprises a shaft having a proximal end and a distal end, and a slot located near the distal end of the shaft, the slot including a radial portion extending radially into the shaft to an inner terminal end, and an axial portion extending axially along the shaft from the inner terminal end of the radial portion.

15. The delivery system of claim 14, wherein the association loop hooks onto the slot by sliding radially along the radial portion and distally along the axial portion.

16. A sling assembly delivery kit comprising:
    a sling assembly having,
      a sleeve having a first end and a second end,
      a sling residing, at least partially, within the sleeve,
      a dilator having a first end and a second end attached to the first end of the sleeve,
      an association loop extending into the second end of the dilator and located at a first end of the sling assembly;
      a spring loaded mounting arrangement to enable the association loop to extend and retract axially relative to the dilator; and
    a first delivery device onto which the first association loop may be hooked.

17. The kit of claim 16 comprising,
    second association loop located at a second end of the sling assembly, sized and shaped to be hooked onto the first device.

18. The kit of claim 16 comprising,
    a second association loop located at a second end of the sling assembly and
    a second delivery device onto which the second association loop may be hooked.

* * * * *